US012699078B2

(12) United States Patent
Natarajan et al.

(10) Patent No.: US 12,699,078 B2
(45) Date of Patent: Aug. 4, 2026

(54) SYSTEMS, APPARATUSES, METHODS, AND COMPUTER PROGRAM PRODUCTS FOR EMISSIONS QUANTIFICATION

(71) Applicant: Honeywell International Inc., Charlotte, NC (US)

(72) Inventors: Ramesh Murugan Natarajan, Chennai (IN); Shahrul Azman Bin Zainal Abidin, Kajang (MY); Madhukar Gundappa Madhavamurthy, Bangalore (IN)

(73) Assignee: Honeywell International Inc., Charlotte, NC (US)

( * ) Notice: Subject to any disclaimer, the term of this patent is extended or adjusted under 35 U.S.C. 154(b) by 731 days.

(21) Appl. No.: 18/169,450

(22) Filed: Feb. 15, 2023

(65) Prior Publication Data

US 2024/0272133 A1     Aug. 15, 2024

(51) Int. Cl.
*G01N 33/00* (2006.01)

(52) U.S. Cl.
CPC ..... *G01N 33/0062* (2013.01); *G01N 33/0068* (2024.05)

(58) Field of Classification Search
CPC .......... G01N 33/0062; G01N 33/0068; G01N 33/004; G01N 33/0031; G01N 33/0004; G01N 30/72; G01N 30/8693; G01N 30/8679; G01N 21/359; G01N 21/3504; G01N 2030/025; G01N 2021/1793; G05B 19/41875; Y02P 90/84; Y02P 30/00; G01J 3/443

USPC ........ 73/23.2, 1.06, 31.01; 356/302; 702/24, 702/22, 23, 32, 30, 127, 104, 182, 181, 702/108, 189, 33, 2
See application file for complete search history.

(56) References Cited

U.S. PATENT DOCUMENTS

| | | | | |
|---|---|---|---|---|
| 7,865,315 | B2 * | 1/2011 | Greving | G01N 23/2251 |
| | | | | 702/34 |
| 10,203,311 | B2 * | 2/2019 | Risk | G01P 13/02 |
| 2009/0132193 | A1 * | 5/2009 | Greving | G01N 3/068 |
| | | | | 702/98 |
| 2019/0033281 | A1 * | 1/2019 | Mou | G01N 33/0037 |
| 2019/0277731 | A1 * | 9/2019 | Hur | G01N 1/2273 |
| 2020/0116687 | A1 * | 4/2020 | Pratt | G01N 33/0062 |
| 2023/0305547 | A1 * | 9/2023 | Avadhani | G05B 23/0216 |
| 2024/0127439 | A1 * | 4/2024 | Aital | A61B 5/0013 |
| 2024/0143467 | A1 * | 5/2024 | Kulkarni | G01N 33/0006 |

* cited by examiner

*Primary Examiner* — Jeffrey P Aiello
(74) *Attorney, Agent, or Firm* — Alston & Bird LLP

(57) ABSTRACT

Methods, apparatuses, and computer program products for generating optimized emissions quantification are provided. For example, a computer-implemented method may include identifying a first emissions data and a second emissions data associated with a plant. The first emissions data may be associated with first emissions data acquisition level of a plurality of emissions data acquisition levels and the second emissions data may be associated with a second emissions data acquisition level of the plurality of emissions data acquisition levels. The method may further include generating using a reconciliation model and based on the first emissions data and the second emissions data, optimized emissions quantification. The optimized emissions quantification may reflect reconciled emissions data with respect to the first emissions data and the second emissions data.

18 Claims, 7 Drawing Sheets

SYSTEMS, APPARATUSES, METHODS, AND COMPUTER PROGRAM PRODUCTS FOR EMISSIONS QUANTIFICATION

TECHNICAL FIELD

Embodiments of the present disclosure generally relate to quantifying emissions in operational systems, and specifically quantifying emissions based on data from various sources.

BACKGROUND

Various embodiments of the present disclosure address technical challenges related to quantifying emissions in operational systems, such as plants. Through applied effort, ingenuity, and innovation, Applicant has solved problems relating to quantifying emissions in operational systems by developing solutions embodied in the present disclosure, which are described in detail below.

BRIEF SUMMARY

In general, embodiments of the present disclosure provide methods, apparatus, systems, computing devices, computing entities, and/or the like for generating optimized emissions quantification. Other implementations for generating optimized emissions quantification will be, or will become, apparent to one with skill in the art upon examination of the following figures and detailed description. It is intended that all such additional implementations be included within this description be within the scope of the disclosure, and be protected by the following claims.

In accordance with a first aspect of the disclosure, a computer-implemented method is provided. In one example embodiment, the computer-implemented method comprises: identifying a first emissions data and a second emissions data associated with a plant, wherein the first emissions data is associated with first emissions data acquisition level of a plurality of emissions data acquisition levels and the second emissions data is associated with a second emissions data acquisition level of the plurality of emissions data acquisition levels; generating, using a reconciliation model and based on the first emissions data and the second emissions data, optimized emissions quantification, wherein the optimized emissions quantification reflects reconciled emissions data with respect to the first emissions data and the second emissions data; and initiating the performance of one or more prediction-based actions based at least in part on the optimized emissions quantification.

Additionally or alternatively, in some embodiments of the example computer-implemented method, initiating the performance of the one or more prediction-based actions comprises generating an emissions report based on the optimized emissions quantification.

Additionally or alternatively, in some embodiments of the example computer-implemented method, the first emissions data and the second emissions data are associated with substantially the same timestamp.

Additionally or alternatively, in some embodiments of the example computer-implemented method, identifying the first emissions data and the second emissions data comprises receiving emissions data associated with the plant; identifying the second emissions data from the emissions data; determining a timestamp associated with the second emissions data; and identifying the first emissions data from the emissions data based on the timestamp associated with the second emissions data.

Additionally or alternatively, in some embodiments of the example computer-implemented method, generating the optimized emissions quantification comprises determining a difference measure between the first emissions data and the second emissions data; and responsive to determining that the difference measure is a qualifying difference measure, generating the optimized emissions quantification based on the difference measure.

Additionally or alternatively, in some embodiments of the example computer-implemented method, generating the optimized emissions quantification based on the difference measure comprises applying the difference measure to the first emissions data.

Additionally or alternatively, in some embodiments of the example computer-implemented method, generating the optimized emissions quantification based on the difference measure comprises applying a first portion of the difference measure to the first emissions data; and applying a second portion of the difference measure to the second emissions data.

Additionally or alternatively, in some embodiments of the example computer-implemented method, applying the difference measure to the first emissions data comprises applying the difference measure to one or more portions of the first emissions data based at least in part on weights associated with the one or more portions of the first emissions data.

Additionally or alternatively, in some embodiments of the example computer-implemented method, the first emissions data comprises a set of source-based emissions data; each data value in the set of source-based emissions data is associated with an emissions source category of a plurality of emissions source categories for the plant and corresponds to a portion of the first emissions data; and an aggregate of the set of source-based emissions data represents a first total emissions for the plant.

Additionally or alternatively, in some embodiments of the example computer-implemented method, the second emissions data comprise site-based emissions data and represents a second total emissions for the plant.

Additionally or alternatively, in some embodiments of the example computer-implemented method, the reconciliation model comprises a machine learning model trained based at least in part on one or more of historical operational data or historical emissions data.

In accordance with a second aspect of the disclosure, an apparatus is provided. In one example, the apparatus comprises at least one processor and at least one non-transitory memory comprising program code stored thereon. The at least one non-transitory memory and the program code are configured to, with the at least one processor, causes the apparatus to perform any one of the example computer-implemented methods described herein.

In accordance with a third aspect of the disclosure a computer program product is provided. In one example embodiment, the computer program product comprises at least one non-transitory computer-readable storage medium having computer-readable program code portions stored therein. The computer-readable program code portions comprise an executable portion configured to perform any one of the example computer-implemented methods described herein.

It should be appreciated that any and/or all aspects and/or operations of the example computer-implemented methods described herein may be combinable with any other of the aspects and/or operations of any other of the example computer-implemented methods described herein.

The above summary is provided merely for the purpose of summarizing some example embodiments to provide a basic understanding of some aspects of the present disclosure. Accordingly, it will be appreciated that the above-described embodiments are merely examples and should not be construed to narrow the scope or spirit of the present disclosure in any way. It will be appreciated that the scope of the present disclosure encompasses many potential embodiments in addition to those here summarized, some of which will be further described below. Other features, aspects, and advantages of the subject will become apparent from the description, the drawings, and the claims.

BRIEF DESCRIPTION OF THE DRAWINGS

Figure 1:
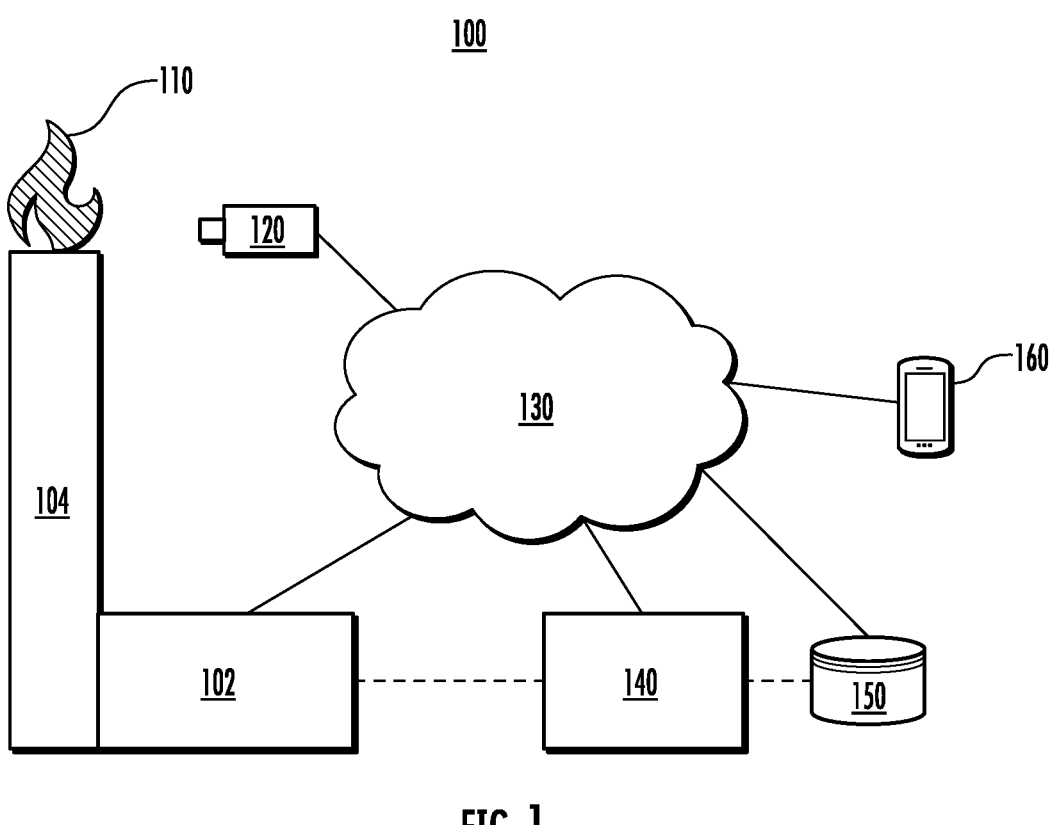
Figure 2:
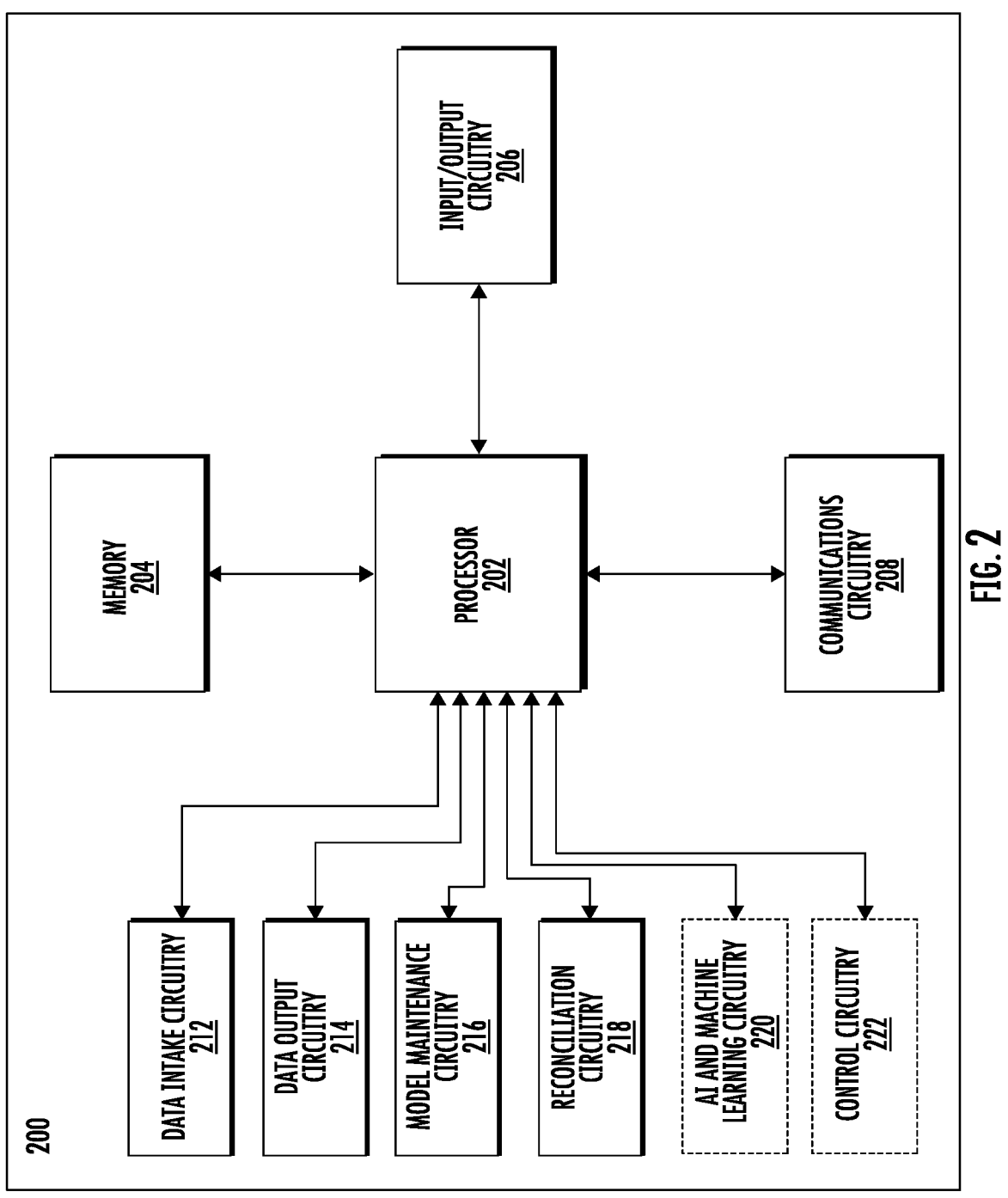
Figure 3:
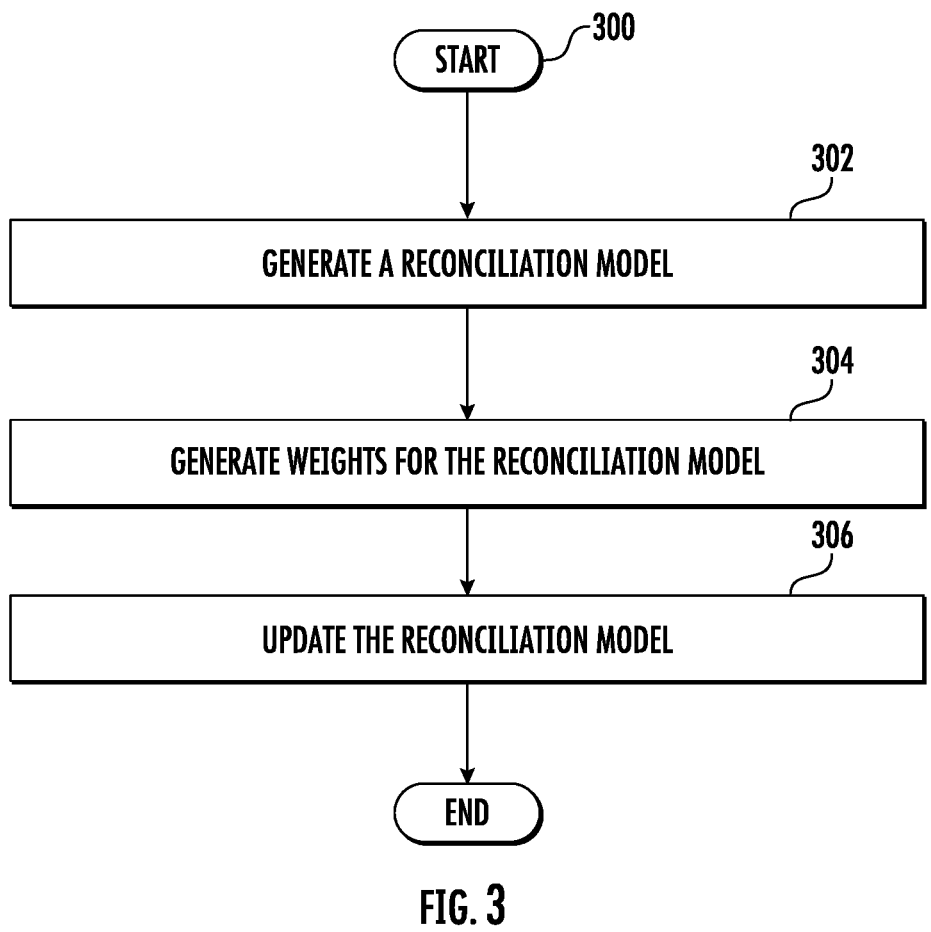
Figure 4:
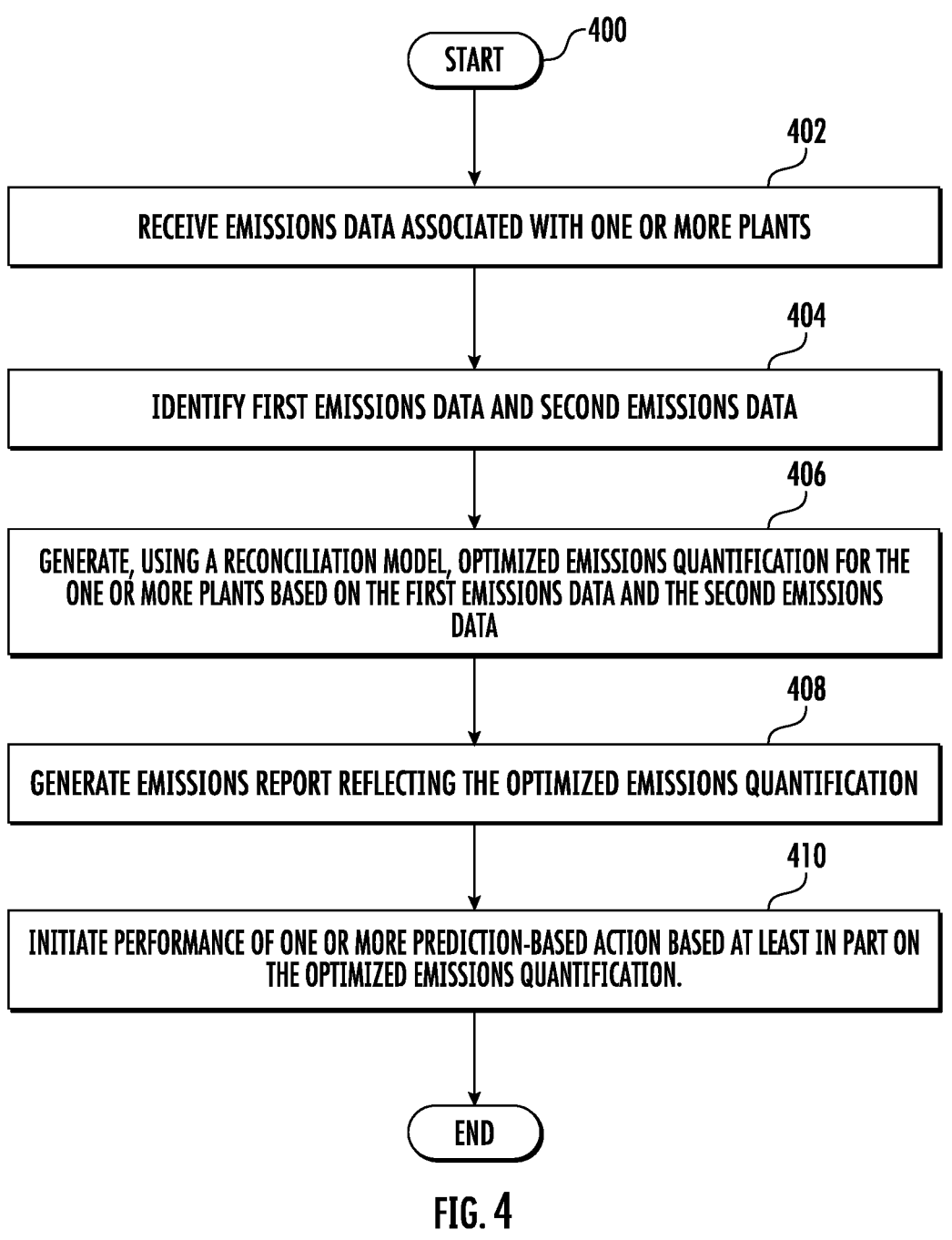
Figure 5:
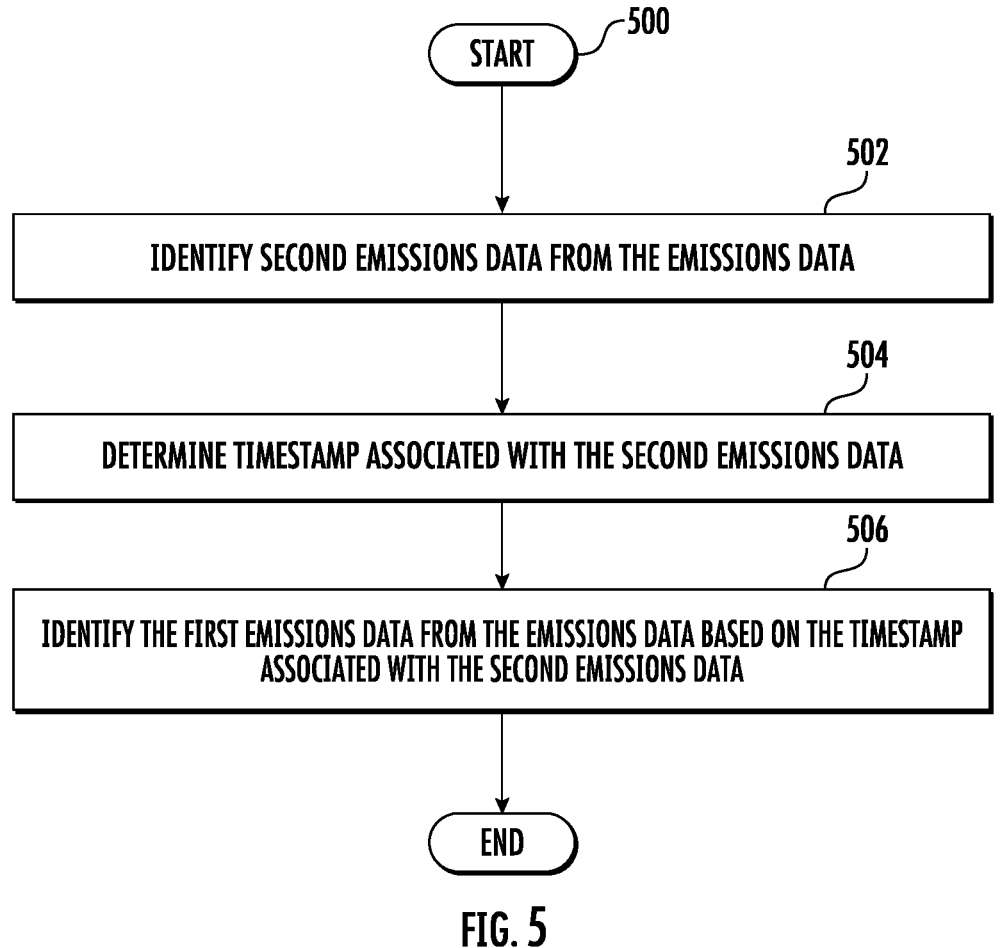
Figure 6:
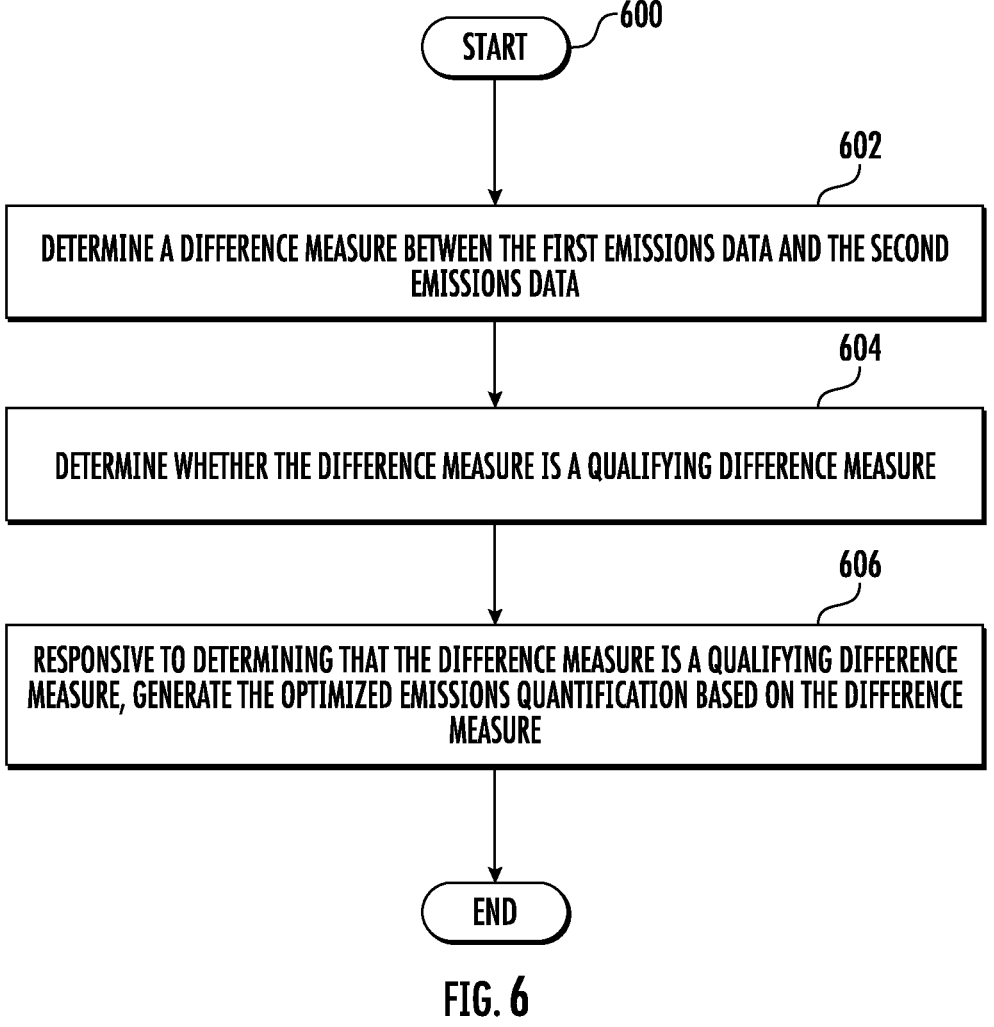
Figure 7:
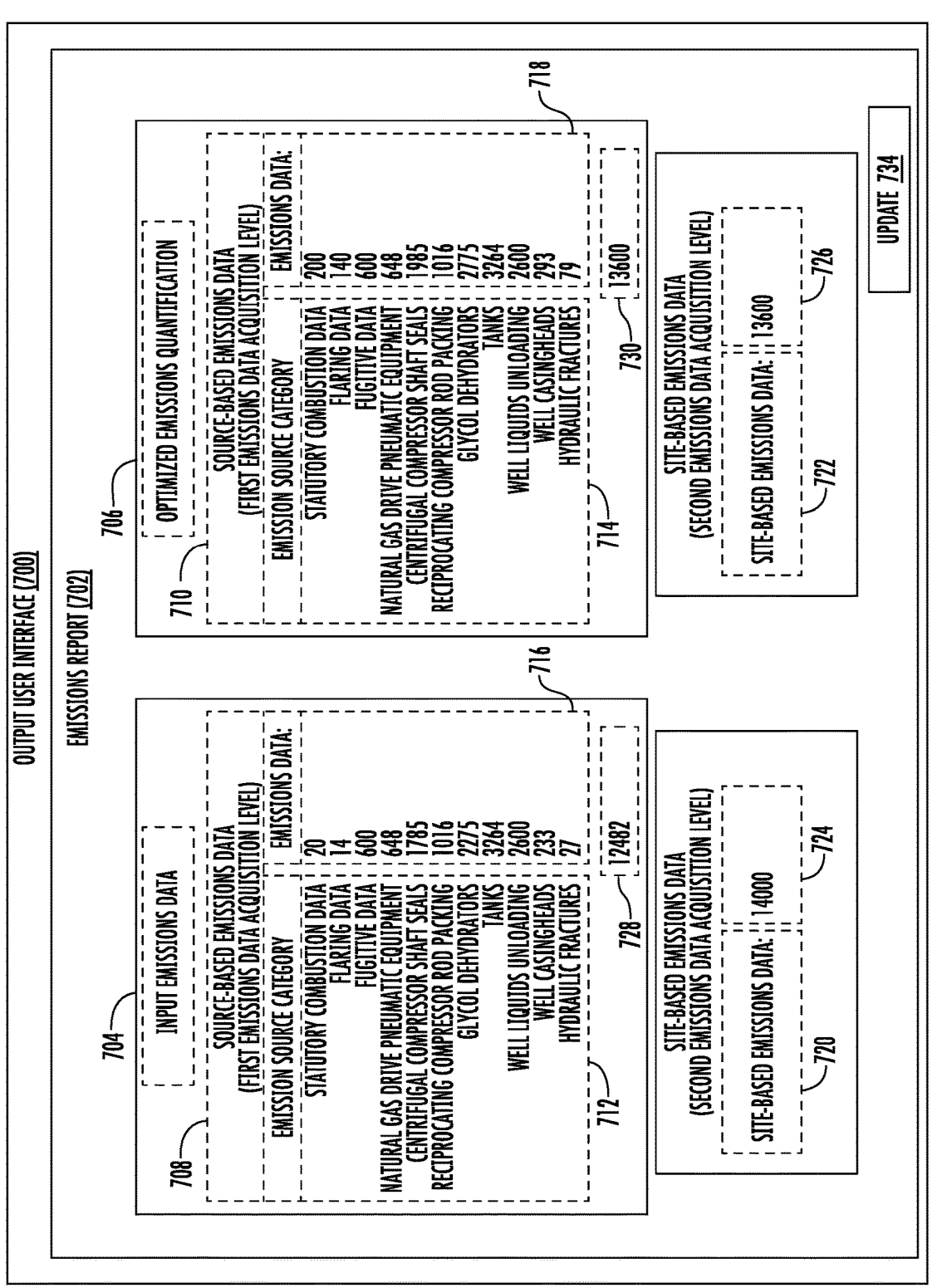

Having thus described the embodiments of the disclosure in general terms, reference now will be made to the accompanying drawings, which are not necessarily drawn to scale, and wherein:

FIG. 1 illustrates an exemplary block diagram of an environment in which embodiments of the present disclosure may operate;

FIG. 2 illustrates an exemplary block diagram of an example apparatus that may be specially configured in accordance with at least one example embodiment of the present disclosure;

FIG. 3 illustrates a flowchart including example operations of an example process for performing configuration operation(s) associated with generating optimized emissions quantification in accordance with at least one example embodiment of the present disclosure;

FIG. 4 illustrates a flowchart including operational blocks of an example process for generating optimized emissions quantification in accordance with at least one example embodiment of the present disclosure;

FIG. 5 illustrates a flowchart including operational blocks of an example process for identify matching emissions data in accordance with at least one example embodiment of the present disclosure;

FIG. 6 illustrates a flowchart including operational blocks of an example process for generating optimized emissions quantification based on a difference measure in accordance with at least one example embodiment of the present disclosure;

FIG. 7 is an illustrates an operational example of an output user interface in accordance with at least some example embodiments of the present disclosure.

DETAILED DESCRIPTION

Some embodiments of the present disclosure now will be described more fully hereinafter with reference to the accompanying drawings, in which some, but not all, embodiments of the disclosure are shown. Indeed, embodiments of the disclosure may be embodied in many different forms and should not be construed as limited to the embodiments set forth herein, rather, these embodiments are provided so that this disclosure will satisfy applicable legal requirements. Like numbers refer to like elements throughout.

As used herein, the term "comprising" means including but not limited to and should be interpreted in the manner it is typically used in the patent context. Use of broader terms such as comprises, includes, and having should be understood to provide support for narrower terms such as consisting of, consisting essentially of, and comprised substantially of.

The phrases "in one embodiment," "according to one embodiment," "in some embodiments," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that a specific component or feature is not required to be included or to have the characteristic. Such a component or feature may be optionally included in some embodiments, or it may be excluded.

The use of the term "circuitry" as used herein with respect to components of a system or an apparatus should be understood to include particular hardware configured to perform the functions associated with the particular circuitry as described herein. The term "circuitry" should be understood broadly to include hardware and, in some embodiments, software for configuring the hardware. For example, in some embodiments, "circuitry" may include processing circuitry, communication circuitry, input/output circuitry, and the like. In some embodiments, other elements may provide or supplement the functionality of particular circuitry. Alternatively or additionally, in some embodiments, other elements of a system and/or apparatus described herein may provide or supplement the functionality of another particular set of circuitry. For example, a processor may provide processing functionality to any of the sets of circuitry, a memory may provide storage functionality to any of the sets of circuitry, communications circuitry may provide network interface functionality to any of the sets of circuitry, and/or the like.

The term "electronically coupled," "electronically coupling," "electronically couple," "in communication with," "in electronic communication with," or "connected" in the present disclosure refers to two or more elements or components being connected through wired means and/or wireless means, such that signals, electrical voltage/current, data and/or information may be transmitted to and/or received from these elements or components.

The term "emissions data acquisition level" as used herein may refer to electronically managed attribute that describes a level associated with or otherwise assigned to a method of quantifying emissions data and/or reporting emissions amount.

The term "optimized emissions quantification" as used herein may refer to a measure of an amount of emission of a gas(es) with respect to a particular plant or multiple plants associated with, for example, an enterprise. In some embodiments, optimized emissions quantification may reflect an emissions amount for a particular individual gas. In some embodiments, optimized emissions quantification may reflect an emissions amount for multiple individual gases represented in a unified manner.

Overview

Example embodiments disclosed herein address technical challenges associated with systems, apparatuses, methods, and computer program products for optimized quantification of emissions, such as optimized quantification of greenhouse gas emissions in operational systems, such as plants. As would be understood by one skilled in the field to which this disclosure pertains, there are numerous example scenarios in which a user may use systems, apparatuses, methods, and computer program products for optimized quantification of greenhouse gas emissions in operational systems.

In many applications, systems, apparatuses, methods, and computer program products, quantification of emissions, in operational systems are necessary. For example, for a variety of reasons, businesses, enterprises, and/or the like, may need to track emissions of greenhouse gases (e.g., methane, carbon dioxide, nitrous oxide, and/or other greenhouse gases) that occur during commercial/industrial activities, such as oil and natural gas production, heating, electricity generation, and manufacturing. The noted greenhouse gas emissions amount can be calculated at various levels ranging from an enterprise level (e.g., across an entire organization) to an individual asset level. In some examples, the emissions amount for a given greenhouse gas with respect to a plant or multiple plants (e.g., multiple plants associated with an enterprise) is calculated based on total emissions (e.g., total methane emission, total nitrous oxide emissions, and/or the like) of the given plant. For example, for an operational system such as a plant (e.g., an operating plant), the emissions for a given greenhouse gas may be calculated as a total amount of the greenhouse gas emissions produced by the operational system. As another example, the total amount of emissions of a given gas produced by the operational system may be calculated as a total amount over a time period (e.g., total amount of emissions per hour). Plant emissions, such as methane emissions and other greenhouse gases, can be calculated using a variety of devices (e.g., sensors) and/or techniques for measuring or estimating emissions. These devices and/or techniques may be associated with various approaches for capturing emissions data (e.g., bottom-up approach, top-down approach, and/or the like).

In some examples, it is necessary for many enterprises to track greenhouse gas emissions in order to meet regulatory and other requirements. Many enterprises, such as corporations that may own and/or operate one or more buildings and/or plants (e.g., industrial plants, such as oil wells, oil refineries, chemical plants, natural gas processing plants, etc.) have made sustainability commitments to their shareholders, customers, regulators, and/or the public in which the enterprises have committed to achieving target greenhouse emissions goal(s), such as reduced methane emissions, reduce nitrous oxide emissions, net zero carbon emissions, and/or the like by a planned date. As such, in some examples, it is necessary for enterprises to accurately track and report their plant emissions in order to ensure that their plant(s) are meeting the various milestones (e.g., near-term and long-term emissions goals). Moreover, in some examples, it is necessary for enterprises to accurately track and report their plant emissions in order to avoid penalties and fines. For example, in some examples, if an enterprise reports inaccurate plant emissions, substantial penalties and fines may be imposed on the enterprise. Accordingly, in some examples, when an enterprise reports plant emissions, it is necessary for the enterprise to report accurate plant emissions. Moreover, in some examples, it is necessary that an enterprise indicate/show the reliability of the reported plant emissions.

However, the presence of a large number of emissions data (e.g., emissions measurements, emissions estimates) obtained from various measuring devices and/or techniques for measuring greenhouse gas emissions; the varying accuracy and/or reliability level of various portions of the emissions data and/or measuring devices; the complex relationship between portions of the emissions data (e.g., emissions data captured using bottoms-up approach relative to emissions data captured using top-down approach, and varying timestamp associated with different portions of the emissions data to name a few); and external factors (e.g., environmental factors) complicates effective and computationally efficient greenhouse gas emissions quantification and reporting. Accordingly, a need exists for efficient and accurate quantification and reporting of greenhouse emissions that accounts for the noted factors (e.g., emissions data size, varying timestamp, external factors, variation in the reliability and the accuracy of the measuring devices and/or techniques used in capturing the emissions data).

Embodiments of the present disclosure provide for generating efficient and accurate greenhouse emissions quantification and reporting to enable more accurate and efficient tracking and reporting of greenhouse gas emissions, which in turn enables efficient and effective greenhouse gas emissions reduction measures and facilitates achievement of emissions goal(s), for example, embodying prediction-based actions. Example embodiments provide for generating optimized emissions quantification and reporting utilizing a particular model-based framework that specifically incorporates many of the (e.g., all of the) important factors for the model to ensure accurate and improved generation of reports, for example, that includes accurate emissions quantification of one or more individual greenhouse gases and/or combined greenhouse gases. For example, in embodiments, emissions quantification for a plant may comprise emissions amount for one or more individual greenhouse gases (e.g., methane, nitrous oxide, and/or other gases). Additionally or alternatively, in embodiments, emissions quantification for a plant may comprise emissions amount for multiple individual greenhouse gases emitted by the plant and may be represented, for example, in terms of carbon dioxide equivalent (e.g., a total amount of carbon dioxide determined based on the multiple greenhouse gases emissions amount). In some embodiments, an emissions report for a plant may comprise optimized emissions quantification that includes emissions amount for one or more individual gases and/or emissions amount for multiple greenhouse gases (e.g. represented as a combined amount of carbon dioxide amount). For example, in some embodiments, emissions amount for each of one or more greenhouse gases may be determined and converted into carbon dioxide amount based on one or more of a variety of techniques (e.g., based on greenhouse global warming potential, as a non-limiting example).

One or more embodiments of the present disclosure utilize a reconciliation model specially configured to reconcile (e.g., continuously, periodically, predetermined intervals, and/or the like), for a given greenhouse gas, emissions data obtained from various data sources and/or associated with various measurement/estimation techniques. By doing so, example embodiments of the present disclosure improve accuracy of emissions quantification and reporting—for example, by utilizing a specially configured reconciliation model that reconciles emissions data from various sources while effectively capturing the various factors associated with the emissions data. This in turn ensures, as non-limiting examples, that operational and/or physical changes made (e.g., to measuring devices, to a plant, control system, and/or the like) in response to generated emissions quantification and/or report are not erroneous. Further, by utilizing a particular model-based framework that ensures with reasonable certainty that generated emissions quantification and report reflect accurate emissions amount in light of the complex relationship of the various factors associated with the emissions data, one or more embodiments of the present disclosure: (i) reduces or eliminates the computational operations that would otherwise be needed to generate updated emissions quantification or report; and (ii) reduces or eliminates the need for additional storage resources, which in turn improves storage efficiency of performing emissions quantification and reporting.

In example embodiments, optimized greenhouse gas emissions quantification for a plant, for example, for individual greenhouse gases or combined greenhouse gases, is generated based on emissions data obtained from a variety of data sources. Additionally, in example embodiments, optimized emissions quantification is generated based on historical data describing how a system or plant has operated in the past, past emissions amount for the system or plant, and/or projected production parameters for determining and/or describing how a plant or operational system will be operated for a given period of time. In one example, historical greenhouse gas emissions measurements corresponding to past operation of a system under certain operating conditions and/or production parameters may be used to reconcile and/or predict greenhouse gas emissions amount for current or future operation of the same system under the same or similar operating conditions and/or production parameters.

Example Systems and Apparatuses

Embodiments of the present disclosure herein include systems, apparatuses, methods, and computer program products configured for and to perform one or more operations for emissions quantification and reporting. It should be readily appreciated that the embodiments of the apparatus, systems, methods, and computer program product described herein may be configured in various additional and alternative manners in addition to those expressly described herein.

FIG. 1 illustrates an exemplary block diagram of an environment 100 in which embodiments of the present disclosure may operate. Specifically, FIG. 1 illustrates a plant 102 that may be associated with a flare stack 104 ("stack 104"). In some embodiments, the plant 102 embodies a processing plant associated with a particular operational goal. For example, in some embodiments, the plant embodies a processing plant including any number of processing unit(s) that, alone or in combination, perform a particular industrial process. In some embodiments, the plant 102 includes or embodies an oil refinery, petrochemical plant, chemical processing plant, or other plant that converts one or more ingredient(s) into a final product by performing particular operations that utilize, process, manipulate, and/or otherwise transform the ingredient(s). It will be appreciated that the depicted and described plant 102 defines non-limiting examples of components and/or operation of particular processing plant(s) and should not limit the scope and spirit of the disclosure to merely these configuration(s). For example, in some embodiments, the plant 102 includes the stack 104, while in other embodiments the plant 102 may not include any such stack.

In some embodiments, the stack 104 is embodied as part of the plant 102, for example as a processing unit thereof. For example, in some embodiments, the stack 104 may be embodied as a processing unit of one or more types of processing units of the plant 102. The stack 104 may be used to flare and/or vent one or more gases. These gases may include, but are not limited to, greenhouse gases. Flaring of gases may generate a flame 110. The flame 110 of a stack 104 may be observed, measured, analyzed by, and/or the like by one or more sensors 120 in accordance with operations and/or functions described herein. Additionally and/or alternatively, various processing units of the plant that are not a stack may be observed, measured, analyzed by, and/or the like by the one or more sensors 120 in accordance with operations and/or functions described herein. One or more of the sensors 120 may generate and/or transmit sensor data across a network 130 to an emissions quantification system 140. The emissions quantification system 140 may be electronically and/or communicatively coupled to one or more operational systems, for example one or more of the plants 102, one or more databases 150, and one or more user devices 160. In some embodiments, a plant 102 embodies or includes a different type of processing plant, and/or does not include the flare stack 104, as discussed above. For example, in some embodiments, the plant 102 includes any number of processing units that each perform different tasks for producing a final product (e.g., a blended, constructed, or otherwise combined product) from one or more input ingredients. One or more of these processing units, for example, may include components and/or sub-components that are a source of greenhouse gas emissions.

The plant 102 may, for example, be a processing plant that receives and processes ingredients as inputs to create a final product, such as a hydrocarbon processing plant. The plant 102 may generate waste gasses. In various embodiments, waste gasses may be released to atmosphere, such as through a stack 104. Alternatively, waste gases may be flared when being released to atmosphere. Additionally, or alternatively, flaring and venting of gases may occur at locations other than a stack 104. For example, smaller quantities of gases at other locations may be released or may unintentionally leak into the atmosphere. In some embodiments, locations other than a stack 104 where gases may be vented and/or flared and/or where gases may unintentionally leak may include well heads, safety release valves, pipe headers, and/or the like. These other locations may also be observed, measured, analyzed by, and/or the like by the one or more sensors 120.

The plant 102 in some embodiments includes any number of individual processing units. The processing units may each embody an asset of the plant 102 that performs a particular function during operation of the plant 102. For example in the example context of a hydrocarbon processing plant, a refinery plant, a drilling plant, and/or a fracking plant embodying the plant 102, the processing units may include one or more crude processing units, a hydrotreating units, isomerization units, vapor recovery units, catalytic cracking units, aromatics reduction units, visbreaker units, storage tank units, blender units, pump units, flash venting units, compressor units, cooler units (e.g., air cooler units), sensor units, flare units (e.g., the stack 104), and/or the like that perform a particular operation for transforming, storing, and/or otherwise handling one or more input ingredient(s). In some embodiments, the one or more sensor units may include one or more greenhouse gas sensors, flow rate sensors, temperature sensors, pressure sensors, humidity sensors, image sensors, density sensors, material composition sensors (e.g., spectrometers, spectrophotometers, etc.), and/or the like.

In some embodiments, each individual unit embodying a component of the plant 102 is associated with a determinable location. The determinable location of a particular unit in some embodiments represents an absolute position (e.g., GPS coordinates, latitude and longitude locations, and/or the like) or a relative position (e.g., a point representation of the location of a unit from a local origin point corresponding to the plant 102). In some embodiments, a unit includes or otherwise is associated with a location sensor and/or software-driven location services that provide the location data representing the location corresponding to that unit. In other embodiments the location of a unit is stored and/or otherwise predetermined within a software environment, provided by a user and/or otherwise determinable to one or more systems, for example including the emissions quantification system 140.

Additionally or alternatively, in some embodiments, the plant 102 itself is associated with a determinable location. The determinable location of the plant 102 in some embodiments represents an absolute position (e.g., GPS coordinates, latitude and longitude locations, an address, and/or the like) or a relative position of the plant (e.g., an identifier representing the location of the plant 102 as compared to one or more other plants, an enterprise headquarters, or general description in the world for example based at least in part on continent, state, or other definable region). In some embodiments, the plant 102 includes or otherwise is associated with a location sensor and/or software-driven location services that provide the location data corresponding to the plant 102. In other embodiments, the location of the plant 102 is stored and/or otherwise determinable to one or more systems, for example including the emissions quantification system 140.

The flame 110 may be associated with flaring. Flaring involves the igniting and burning of concentrations of flammable gases. A gas may be comprised of a plurality of concentrations of individual gases, and some of these concentrations of individual gases may be flammable. Alternatively, a gas may be comprised of a concentration of an individual gas, which may or may not be flammable. In some embodiments, a gas may contain greenhouse gases, such as hydrocarbons. The hydrocarbons may be ignited by an ignition source, such as a pilot flame, when the gas passes by the ignition source. The ignited gas(es) may be referred to as flares, and this process may be referred to as flaring. In various embodiments, flaring may occur at the flare stack 104, which may be at a high level of elevation from one or more other components of a plant 102, process area, piping, and the like associated with a site (e.g., a particular plant). While FIG. 1 illustrates a flame 110, it will also be appreciated that by removing or omitting an ignition source, such as a pilot flame, gas(es) may be vented without flaring.

The one or more sensors 120 may include sensors to detect, measure, and/or analyze data associated with operation of a plant or multiple plants, for example, the plant 102. In one such example context, the sensors detect, measure, and/or analyze a flame 110 and/or a gas emission, for example associated with a flaring, a venting, unintentional leaking, and/or other emissions sources. For example, in some embodiments, the sensors are configured to detect, measure, and/or analyze emissions from one or more processing units that results from the operations of the processing unit, whether sensed from within the processing unit itself, a link between the processing unit and another, a flare stack, and/or the like. In some embodiments, sensors may include a camera, which may be configured to capture images and/or video in one or more spectrums of light. For example, a camera may be configured to capture images and/or video in the visible spectrum. Additional, and/or alternatively, a camera may be configured to capture images and/or video in the infrared spectrum. It will be appreciated that any number of sensor(s), sensor type(s), and/or the like may be utilized detect, measure, and/or analyze a gas emission of a particular plant and/or multiple plants, or otherwise to monitor operations of a particular plant, and/or multiple plant(s). For example the sensors 120 may include or embodied by one or more of a camera, a satellite, a drone, an aircraft, a sampling measurement device, an ultrasonic device, and/or the like. A sensor of the sensors 120 may be configured for direct measurement of an amount of greenhouse gas emitted from an emissions source and/or an area of a plant. Additionally or alternatively, a sensor of the sensors 120 may be configured for indirect measurement of amount of greenhouse gas emitted from an emissions source and/or an area of a plant. For example, a sensor of the sensors 120 may be utilized in combination with emission factor(s) and/or other emissions estimation methods. Additionally or alternatively still, the plant 102 may comprise one or more of the sensors 120 for detecting various operating conditions of the plant 102 and/or generating operating conditions data indicative of the detected operating conditions.

In some embodiments, at least one sensor of the one or more sensors 120 may comprise a source-based sensor. Additionally, in some embodiments, at least one sensor of the one or more sensors 120 may comprise a site-based sensor. A source-based sensor may describe a sensor that corresponds to a bottom-up approach for quantifying (e.g., measuring and/or estimating) emissions, while a site-based sensor may describe a sensor that corresponds to a top-down approach for quantifying (e.g., measuring and/or estimating) emissions. In some embodiments, quantified emissions reflect an emissions amount for an individual greenhouse gas, wherein an emissions report may include emissions quantification for one or more individual greenhouse gases. In some embodiments quantified emissions reflect an emissions amount for combined greenhouse gases, wherein an emissions report may include emissions quantification for combined greenhouse gases. A bottom-up approach may describe techniques/methods for quantifying emissions based at least in part on measuring the emissions at the source of the emissions (e.g., vent, pump, valve, and/or the like). A bottom-up approach may utilize technology (e.g., measuring devices) incorporating a sensor(s) (e.g., source-based sensor(s)) located proximate to the source of the emission. In some embodiments, a source-based sensor may be configured for quantifying the emissions in a portion (e.g., an area) of the plant. In some embodiments, emissions data collected (e.g., retrieved and/or received) from one or more source-based sensors may be aggregated to represent a total emissions for the plant 102 based on a bottom-up approach. A top-down approach may describe techniques/methods for quantifying emissions based at least in part on measuring the emissions distal from the source of the emissions, for example, measuring concentration of the emitted gas in the atmosphere over a given area (e.g., measuring the atmosphere above a plant). A top-down approach may utilize technology such as, but not limited to, aircrafts, drones, and satellites incorporating sensor(s) (e.g., site-based sensor(s)) located at a substantial distance from the source of the emission. In some embodiments, a site-based sensor may be configured for quantifying the emissions at a plant level, for example, at an entire plant-level. For example, in some embodiments, emissions data collected (e.g., retrieved, received) from a sensor, such as a sensor embodied in a satellite, drone, and/or the like, may represent the total emission for the plant 102 based on a top-down approach.

In some embodiments, a sensor of the sensors 120 may be configured to perform or execute one or more operations and/or functions with determining a type, quantity, and/or volume of gas flared and/or emitted. For example, a sensor, such as a camera, may capture both visible light and infrared light to generate images and/or video of flaring. Based on these images and/or video of flaring, the sensor may determine a type of gas being in a flame 110 as well as a volume of gas flared. In another example with a gas emission that is vented and/or leaked and not flared, a sensor, such as a camera, may capture both visible light and infrared light to generate images and/or video of venting and/or leaking. Based on these images and/or video of venting and/or leaking, the camera may determine a type of gas as well as a volume of gas vented and/or leaked. In various embodiments, a sensor of the sensors 120 may generate sensor data (e.g., a camera generating images and/or video) and transmit the sensor data over a network 130. In some embodiments, the sensor data comprise emissions data. In one example, the plant 102 may comprise one or more sensors 120 for measuring methane emissions and/or other greenhouse gas emissions, and generating emissions data indicating the emissions measurements.

The network 130 may be embodied in any of a myriad of network configurations. In some embodiments, the network 130 may be a public network (e.g., the Internet). In some embodiments, the network 130 may be a private a private network (e.g., an internal localized, or closed-off network between particular devices). In some other embodiments, the network 130 may be a hybrid network (e.g., a network enabling internal communications between particular connected devices and external communications with other devices). In various embodiments, the network 130 may include one or more base station(s), relay(s), router(s), switch(es), cell tower(s), communications cable(s), routing station(s), and/or the like. In some embodiments, the network 130 includes one or more user controlled computing device(s) (e.g., a user owned router and/or modem) and/or one or more external utility devices (e.g., Internet service provider communication tower(s) and/or other device(s)). In various embodiments, components of the environment 100 may be communicatively coupled to transmit data to and/or receive data from one another over the network 130. Such configuration(s) include, without limitation, a wired or wireless Personal Area Network (PAN), Local Area Network (LAN), Metropolitan Area Network (MAN), Wide Area Network (WAN), and/or the like.

The emissions quantification system 140 may be located remotely or in proximity of a particular plant, for example the plant 102. In some embodiments, the emissions quantification system 140 is configured via hardware, software, firmware, and/or a combination thereof, to perform data intake of one or more types of data associated with one or more plant(s), for example the plant 102. In some embodiments, the emissions quantification system 140 is configured via hardware, software, firmware, and/or a combination thereof, to generate optimized emissions quantification associated with operation of one or more plants 102 or components thereof. For example, the optimized emissions quantification may represent the amount of emissions for the one or more plants 102 or portions of the one or more plants 102, over a given time period. In some embodiments, the optimized emissions quantification may be associated with two or more emissions data acquisition levels of a plurality of emissions data acquisition levels. For example, the optimized emissions quantification may comprise optimized first emissions data corresponding to a first emissions data acquisition level and optimized second emissions data corresponding to a second emissions data acquisition level. In some examples, a first emissions data acquisition level may be associated with a bottom-up approach, as described above, while a second emissions data acquisition level may be associated with a top-down approach, as described above. In some embodiments, the optimized emissions quantification for the one or more plants 102 comprise reconciled emissions data with respect to emissions data associated with the first emissions data acquisition level and emissions data associated with the second emissions data acquisition level. In various embodiments, emissions data for a plant may include first emissions data associated with and/or corresponding to a first emissions data acquisition level, and second emissions data associated with and/or corresponding to a second emissions data acquisition level. In various embodiments, each of the first emissions data and the second emissions data comprise emissions amount for a given greenhouse gas that is determined (e.g., estimated, calculated, quantified, and/or the like) based on the respective emissions data acquisition level (e.g., first emissions data acquisition level, second emissions data acquisition level). The reconciled emissions data may correspond to emissions from various emissions sources of the one or more plants 102. In some embodiments, the emissions quantification system 140 is configured via hardware, software, firmware, and/or a combination thereof, to generate emissions report(s) based at least in part on the optimized emissions quantification associated with operation of one or more plants 102 and/or components thereof.

Additionally or alternatively, in some embodiments, the emissions quantification system 140 is configured via hardware, software, firmware, and/or a combination thereof, to generate and/or transmit command(s) that control, adjust, or otherwise impact operations of a particular plant or specific component(s) thereof, for example for controlling one or more operations of the plant 102. Additionally or alternatively still, in some embodiments, the emissions quantification system 140 is configured via hardware, software, firmware, and/or a combination thereof, to perform data reporting and/or other data output process(es) associated with monitoring or otherwise analyzing operations of one or more processing plant(s), for example for generating and/or outputting report(s) corresponding to the operations performed via the plant 102. For example, in various embodiments, the emissions quantification system 140 may be configured to execute and/or perform one or more operations and/or functions described herein.

In some embodiments, the emissions quantification system 140 generates emissions quantification using one or more specially configured models, such as a reconciliation model. In some embodiments the emissions quantification system 140, utilizing a reconciliation model, may be configured to formulate and/or optimize one or more reconciliation problems (e.g., optimization problem, and/or the like) associated with the reconciliation model in order to generate optimized emissions quantifications that reflect reconciled emissions data associated with at least two emissions data acquisition levels. As such, in some embodiments, the emissions quantification system 140, utilizing a reconciliation model formulates and/or optimizes one or more reconciliation problems to generate optimized emissions quantification that effectively accounts for measurement errors (e.g., random errors and/or gross errors) associated with emissions data gathered/collected for the one or more plants. For example, in some embodiments, the emissions quantification system 140 may receive or retrieve emissions data from one or more data sources. In some examples, the emissions data includes first emissions data associated with a first emissions data acquisition level such as the first emissions data acquisition level described above, and includes second emissions data associated with a second emissions data acquisition level such as the second emissions data acquisition level described above. The emissions data may be obtained from the one or more sensors 120 and, in some examples, may include errors due to a variety of reasons (including, but not limited to measurement errors such as random errors, errors due to environmental factors such as obstruction of a satellite by a cloud, to name a few). In some embodiments, the emissions quantification system 140, using the reconciliation model and based on the emissions data, may generate an optimized emissions quantification that accounts for the noted errors and reduces the effect of these errors by, for example, detecting outliers in the data; detecting discrepancies between the first emissions data and the second emissions data; and tuning (e.g., adjusting) portions (e.g., some, all) of the emissions data, tuning the reconciliation model and/or tuning one or more sensors (e.g., re-calibration, updating the sensor, and/or the like).

In some embodiments, the emissions quantification system 140 includes one or more application server(s) and/or database server(s) that provide such functionality. Additionally or alternatively, in some embodiments, the emissions quantification system includes one or more client device(s), user device(s), and/or the like, that enable access to the functionality provided via the emissions quantification system 140, for example via a web application, a native application, and/or the like executed on the client device.

The one or more databases 150 may be configured to receive, store, and/or transmit data. In some embodiments, the one or more databases may be associated with sensor data received from sensors 120. The sensor data may include emissions data. In some embodiments, the sensor data may include historical sensor data as well as current and/or real-time sensor data. Additionally or alternatively, the one or more databases 150 may be associated with operations data received from the plant 102, such as from the one or more sensor units of the plant 102. For example, in some embodiments, the one or more databases 150 may be associated with and/or configured to store historical, current (e.g., real-time), and/or planned or projected (e.g., for the future) operational data (e.g., including sensor data, operating conditions data, operating capacity data, and/or operating mode data) for one or more plants 102, emissions data, simulated data (e.g., including simulated emissions and/or simulated operational data), production parameters, and/or emissions reduction strategy information such as emissions reduction plan. In some embodiments a process model may be generated based at least in part on the operations data and may be incorporated into the reconciliation model. In some embodiments, the one or more databases 150 store data associated with multiple individual plant(s), for example multiple plants associated with the same enterprise entity but located in different geographic locations across the world.

The one or more user devices 160 may be associated with users of the emissions quantification system 140. In various embodiments, the emissions quantification system 140 may generate and/or transmit a message, alert, or indication to a user via a user device, for example a user device of the user devices 160. Additionally, or alternatively, a user device, for example a user device of the user devices 160, may be utilized by a user to remotely access an emissions quantification system 140. This may be by, for example, an application operating on the user device, for example a user device of the user devices 160. A user may access the emissions quantification system 140 remotely, including one or more visualizations, reports (e.g., emissions reports), and/or real-time displays.

While FIG. 1 illustrates certain components as separate, standalone entities communicating over the network 130, various embodiments are not limited to this configuration. In other embodiments, one or more components may be directly connected and/or share hardware or the like such that connection(s) over the network 130 are altered and/or rendered unnecessary. For example, in some embodiments, the emissions quantification system 140 may include one or more databases 150, which may collectively be located in or at the plant 102, such that network 130 may not be required.

FIG. 2 illustrates an exemplary block diagram of an example apparatus that may be specially configured in accordance with an example embodiment of the present disclosure. Specifically, FIG. 2 depicts an example computing apparatus 200 ("apparatus 200") specially configured in accordance with at least some example embodiments of the present disclosure. Examples of an apparatus 200 may include, but is not limited to, a sensor of the sensors 120, an emissions quantification system 140, databases 150, and/or a user device, for example a user device of the user devices 160. In some embodiments, the emissions quantification system 140 and/or portion thereof is embodied by one or more system(s), such as the apparatus 200 as depicted in FIG. 2. The apparatus 200 includes processor 202, memory 204, input/output circuitry 206, communications circuitry 208, data intake circuitry 212, data output circuitry 214, model maintenance circuitry 216, reconciliation circuitry 218, optional artificial intelligence ("AI") and machine learning circuitry 220, and optional control circuitry 222. In some embodiments, the apparatus 200 is configured, using one or more of the sets of circuitry 202-208, and 212-222, to execute and perform the operations described herein.

Although components are described with respect to functional limitations, it should be understood that the particular implementations necessarily include the use of particular computing hardware. It should also be understood that in some embodiments certain of the components described herein include similar or common hardware. For example, in some embodiments two sets of circuitry both leverage use of the same processor(s), memory(ies), circuitry(ies), and/or the like to perform their associated functions such that duplicate hardware is not required for each set of circuitry. The use of the term "circuitry" as used herein with respect to components of the apparatuses described herein should therefore be understood to include particular hardware configured to perform the functions associated with the particular circuitry as described herein.

In various embodiments, a device, system, or apparatus, such as apparatus 200 of an emissions quantification system 140 or of a user device, for example a user device of the user devices 160, may refer to, for example, one or more computers, computing entities, desktop computers, mobile phones, tablets, phablets, notebooks, laptops, distributed systems, servers, or the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein. In one embodiment, these functions, operations, and/or processes can be performed on data, content, information, and/or similar terms used herein. In this regard, the apparatus 200 embodies a particular, specially configured computing entity transformed to enable the specific operations described herein and provide the specific advantages associated therewith, as described herein.

Processor 202 or processor circuitry 202 may be embodied in a number of different ways. In various embodiments, the use of the terms "processor" should be understood to include a single core processor, a multi-core processor, multiple processors internal to the apparatus 200, and/or one or more remote or "cloud" processor(s) external to the apparatus 200. In some example embodiments, processor 202 may include one or more processing devices configured to perform independently. Alternatively, or additionally, processor 202 may include one or more processor(s) configured in tandem via a bus to enable independent execution of operations, instructions, pipelining, and/or multithreading.

In an example embodiment, the processor 202 may be configured to execute instructions stored in the memory 204 or otherwise accessible to the processor. Alternatively, or additionally, the processor 202 may be configured to execute hard-coded functionality. As such, whether configured by hardware or software methods, or by a combination thereof, processor 202 may represent an entity (e.g., physically embodied in circuitry) capable of performing operations according to embodiments of the present disclosure while configured accordingly. Alternatively, or additionally, processor 202 may be embodied as an executor of software instructions, and the instructions may specifically configure the processor 202 to perform the various algorithms embodied in one or more operations described herein when such instructions are executed. In some embodiments, the processor 202 includes hardware, software, firmware, and/or a combination thereof that performs one or more operations described herein. In some embodiments, the processor 202 (and/or co-processor or any other processing circuitry assisting or otherwise associated with the processor) is/are in communication with the memory 204 via a bus for passing information among components of the apparatus 200.

As one particular example embodiments, the processor 202 is configured to perform various operations associated with generating optimized emissions quantification and report using at least one specially configured model. In some embodiments, the specially configured model embodies or otherwise comprise a reconciliation model. In some embodiments, the processor 202 includes hardware, software, firmware, and/or a combination thereof, that determines results for one or more problem formulations associated with the reconciliation model. In some embodiments, the reconciliation model generates optimized emissions quantification and report associated with one or more plants 102 based at least in part on emissions data for the one more plants over a given time period. In some embodiments, the emissions data includes emissions data from sensors 120. In some examples, the emissions data comprises at least a first emissions data associated with a first emissions data acquisition level and a second emissions data associated with a second emissions data acquisition level, as described above in connection with FIG. 1. In some embodiments, the first emissions data comprises a set of source-based emissions data, wherein each data value in set of source-based emissions data is associated with an emissions source category. Examples of such emissions source categories include, but not limited to, stationary combustion, flaring, fugitive component and/or equipment leak, natural gas driven pneumatic equipment, centrifugal compressor shaft seals, reciprocating compressor rod packing, glycol dehydrators, tanks, well liquids unloading, well casinghead venting, hydraulic fracture completions, venting, and/or the like. Each data value in the set of source-based emissions data may correspond to a portion of the first emissions data and an aggregate of the set of source-based emissions data may represent a total emissions for the plant 102 in accordance with the first emissions data acquisition level. Additionally or alternatively, still, in some examples, the second emissions data comprises site-based emissions data and may represent a total emissions for the plant 102 in accordance with the second emissions data acquisition level. For example, the site-based emission data may comprise a single data value that is obtained based at least in part on a site-based sensor (e.g., satellite, drones, and/or unmanned aircrafts embodying the site-based sensor).

In some embodiments, generating the optimized emissions quantification and report comprise reconciling the emissions data (e.g., first emissions data and second emissions data) based at least in part on tuning, adjusting, and/or similar words used herein interchangeably, one or more portions of the emissions data (e.g., one or more portions of the first emissions data and/or the second emissions data). In some embodiments, the reconciliation model may be configured to reconcile the emissions data based at least in part on determining discrepancy and/or outliers in the emissions data and adjusting one or more portions of the first emissions data and/or adjusting the second emissions data in accordance with weights associated with the emissions data (e.g., weights assigned to various portions of the first emissions data and second emissions data). In some embodiments, the processor 202 includes hardware, software, firmware, and/or a combination thereof, for generating emissions amount trend data associated with the first emissions data acquisition level and the second emissions data acquisition level, wherein the emissions amount trend data may indicate reduced (e.g., lower) discrepancy between the first emissions data acquisition level and the second emissions data acquisition level with time, For example, the generated emissions amount trend data may indicate, for a given time period relative to previous time periods (e.g., for a given year relative to prior years, for a given month relative to prior months, and/or the like) and based on applying the reconciliating model to emissions data for the previous time periods, reduced discrepancy between emissions data corresponding to the first emissions data acquisition level and emissions data corresponding to the second emissions data acquisition level. Additionally or alternatively, in some embodiments, the processor 202 includes hardware, software, firmware, and/or a combination thereof, that outputs the generated optimized emissions quantification and/or report. Additionally or alternatively, in some embodiments, the processor 202 includes hardware, software, firmware, and/or a combination thereof, that facilitates, based at least in part on the emissions quantification and/or report, one or more of reconfiguration of a measuring device (e.g., sensor thereof), reconfiguration of the operation of at least one component (e.g., equipment); or tuning the reconciliation model.

Memory 204 or memory circuitry embodying the memory 204 may be non-transitory and may include, for example, one or more volatile and/or non-volatile memories. In some embodiments, the memory 204 includes or embodies an electronic storage device (e.g., a computer readable storage medium). In some embodiments, the memory 204 is configured to store information, data, content, applications, instructions, or the like, for enabling an apparatus 200 to carry out various operations and/or functions in accordance with example embodiments of the present disclosure.

Input/output circuitry 206 may be included in the apparatus 200. In some embodiments, input/output circuitry 206 may provide output to the user and/or receive input from a user. The input/output circuitry 206 may be in communication with the processor 202 to provide such functionality. The input/output circuitry 206 may comprise one or more user interface(s). In some embodiments, a user interface may include a display that comprises the interface(s) rendered as a web user interface, an application user interface, a user device, a backend system, or the like. In some embodiments, the input/output circuitry 206 also includes a keyboard, a mouse, a joystick, a touch screen, touch areas, soft keys a microphone, a speaker, or other input/output mechanisms. The processor 202 and/or input/output circuitry 206 comprising the processor may be configured to control one or more operations and/or functions of one or more user interface elements through computer program instructions (e.g., software and/or firmware) stored on a memory accessible to the processor (e.g., memory 204, and/or the like). In some embodiments, the input/output circuitry 206 includes or utilizes a user-facing application to provide input/output functionality to a computing device and/or other display associated with a user.

Communications circuitry 208 may be included in the apparatus 200. The communications circuitry 208 may include any means such as a device or circuitry embodied in either hardware or a combination of hardware and software that is configured to receive and/or transmit data from/to a network and/or any other device, circuitry, or module in communication with the apparatus 200. In some embodiments the communications circuitry 208 includes, for example, a network interface for enabling communications with a wired or wireless communications network. Additionally or alternatively, the communications circuitry 208 may include one or more network interface card(s), antenna(s), bus(es), switch(es), router(s), modem(s), and supporting hardware, firmware, and/or software, or any other device suitable for enabling communications via one or more communications network(s). In some embodiments, the communications circuitry 208 may include circuitry for interacting with an antenna(s) and/or other hardware or software to cause transmission of signals via the antenna(s) and/or to handle receipt of signals received via the antenna(s). In some embodiments, the communications circuitry 208 enables transmission to and/or receipt of data from a user device, one or more sensors, and/or other external computing device(s) in communication with the apparatus 200.

Data intake circuitry 212 may be included in the apparatus 200. The data intake circuitry 212 may include hardware, software, firmware, and/or a combination thereof, designed and/or configured to capture, receive, request, and/or otherwise gather data associated with operations of one or more operational systems (e.g., plants). In some embodiments, the data intake circuitry 212 includes hardware, software, firmware, and/or a combination thereof, that communicates with one or more sensor(s), unit(s), and/or the like within a particular plant to receive particular data associated with such operations of the plant. The data intake circuitry 212 may support such operations for any number of individual plants. Additionally or alternatively, in some embodiments, the data intake circuitry 212 includes hardware, software, firmware, and/or a combination thereof, that retrieves particular data associated with one or more plant(s) from one or more data repository/repositories accessible to the apparatus 200.

AI and machine learning circuitry 220 may be included in the apparatus 200. The AI and machine learning circuitry 220 may include hardware, software, firmware, and/or a combination thereof designed and/or configured to request, receive, process, generate, and transmit data, data structures, control signals, and electronic information for training and executing a trained AI and machine learning model configured to facilitating the operations and/or functionalities described herein. For example, in some embodiments the AI and machine learning circuitry 220 includes hardware, software, firmware, and/or a combination thereof, that identifies training data and/or utilizes such training data for training a particular machine learning model, AI, and/or other model to generate particular output data based at least in part on learnings from the training data. Additionally or alternatively, in some embodiments, the AI and machine learning circuitry 220 includes hardware, software, firmware, and/or a combination thereof, that embodies or retrieves a trained machine learning model, AI and/or other specially configured model utilized to process inputted data. Additionally or alternatively, in some embodiments, the AI and machine learning circuitry 220 includes hardware, software, firmware, and/or a combination thereof that processes received data utilizing one or more algorithm(s), function(s), subroutine(s), and/or the like, in one or more pre-processing and/or subsequent operations that need not utilize a machine learning or AI model.

Data output circuitry 214 may be included in the apparatus 200. The data output circuitry 214 may include hardware, software, firmware, and/or a combination thereof, that configures and/or generates an output based at least in part on data processed by the apparatus 200. In some embodiments, the data output circuitry 214 includes hardware, software, firmware, and/or a combination thereof, that generates a particular report based at least in part on the processed data, for example where the report is generated based at least in part on a particular reporting protocol. In some embodiments, the generated report includes optimized emissions quantification for a plant 102 or multiple plants 102, such as plants associated with a particular enterprise. Additionally or alternatively, in some embodiments, the data output circuitry 214 includes hardware, software, firmware, and/or a combination thereof, that configures a particular output data object, output data file, and/or user interface for storing, transmitting, and/or displaying. For example, in some embodiments, the data output circuitry 214 generates and/or specially configures a particular data output for transmission to another sub-system for further processing. Additionally or alternatively, in some embodiments, the data output circuitry 214 includes hardware, software, firmware, and/or a combination thereof, that causes rendering of a specially configured user interface based at least in part on data received by and/or processing by the apparatus 200.

The model maintenance circuitry 216 includes hardware, software, firmware, and/or a combination thereof, that supports configuration and/or generation of one or more specially configured model(s) utilized to generate optimized emissions quantification and report for one or more plants. In some embodiments, the model maintenance circuitry 216 includes hardware, software, firmware, and/or a combination thereof, that performs one or more configuration operations and/or stores model configuration data with respect to the reconciliation model. In some embodiments, the model maintenance circuitry 216 includes hardware, software, firmware, and/or a combination thereof, that stores the reconciliation model. In some embodiments, the model maintenance circuitry 216 includes hardware, software, firmware, and/or a combination thereof, that updates the reconciliation model. In some embodiments, the model maintenance circuitry 216 includes hardware, software, firmware, and/or a combination thereof, that stores historical optimized emissions quantification and/or report. In some embodiments, the model maintenance circuitry 216 includes hardware, software, firmware, and/or a combination thereof, that updates the optimization model. In some embodiments, the model maintenance circuitry 216 includes hardware, software, firmware, and/or a combination thereof, that receives or retrieves (e.g., from one or more databases) input data for the reconciliation model. In some embodiments, the model maintenance circuitry 216 includes a separate processor, specially configured field programmable gate array (FPGA), or a specially programmed application specific integrated circuit (ASIC).

The reconciliation circuitry 218 includes hardware, software, firmware, and/or a combination thereof, that supports generation of optimized emissions quantification (that accounts for errors in emissions data associated with the operation of corresponding plant(s)) utilizing a reconciliation model. In some embodiments, the reconciliation circuitry 218 includes hardware, software, firmware, and/or a combination thereof, that receives or retrieves emissions data associated with operation of one or more plants (e.g., one or more component(s), product(s), and/or the like of the one or more plants thereof). In some embodiments, the emissions data comprise emissions data generated based on measurement data received from one or more sensors, such as the one or more sensors 120 described above in connection with FIG. 1. In some embodiments, the one or more sensors may comprise source-based sensor(s) and site-based sensor(s).

In an example, a plurality of source-based sensors may be located in strategic locations relative to a given plant 102. As described above, in some embodiments, each individual processing unit embodying a component of the plant 102 is associated with a determinable location. In some embodiments, each source-based sensor is associated with a particular area of a plant based at least in part on the determinable location of the processing unit and/or component embodying the emissions source that the sensor is configured to measure. As such, emissions measurements generated based on a given source-based sensor may be associated with a processing unit, a component, and/or an area of a plant 102 based at least in part on the determinable location associated with the processing unit, the component, and/or the source-based sensor. In some embodiments, each source-based sensor of a plurality of source-based sensors may be strategically located proximate to a source of emission for the plant 102. In some examples, the sensor data received from a respective source-based sensor represents an emissions amount reflecting the emissions from a corresponding emissions source and/or area of the plant 102. In some examples, the sensor data received from a respective source-based sensor may be utilized to estimate the amount of emissions from a corresponding emissions source. As described above in connection with FIG. 1, in some examples, the emissions amount from a source-based sensor may reflect the emissions amount for a particular individual greenhouse gas, while in some examples, the emissions amount from a respective source-based sensor may reflect the emissions amount for multiple greenhouse gases as a unified emissions amount. In some embodiments, emissions data obtained based on sensor data from a given set of one or more source-based sensors may represent the amount of emissions for a given area of the plant 102 with respect to a particular individual greenhouse gas or with respect to multiple greenhouse gases. Additionally or alternatively, in some embodiments, emissions data obtained based on sensor data from one or more sets of source-based sensors may represent the total amount of emissions for an entire plant 102 with respect to a particular individual greenhouse gas or with respect to multiple greenhouse gases. In some embodiments, emissions data obtained from various sensors associated with various areas of a plant may be aggregated to generate a first total emissions for the plant 102 based on a bottom-up approach and correspond to a first emissions data acquisition level.

In some embodiments, one or more site-based sensors (e.g., embodied in a satellite, drone, aircraft, and/or the like) may be employed to generate emissions data that represents the total emissions for the plant 102 with respect to a particular individual greenhouse gas or multiple greenhouse gases reflected as a unified emissions amount. For example, top down-based sensor(s) embodied in a satellite, drone, aircraft, and/or the like, may be used to generate total emissions for a plant that reflects the emissions amount for a particular individual greenhouse gases or reflects the emissions amount for multiple greenhouse gases embodied as a unified emissions amount. In some embodiments, emissions data obtained from a set of one or more top-down based represents a total emissions for the plant 102 based on a top-down approach and correspond to a second emissions data acquisition level. As such in some embodiments, a first total emissions amount for a plant over a given period of time may be generated based on an aggregate of emissions measurements obtained from source-based sensor(s), and a second total emissions amount for the plant over the same given period of time may be generated based on emissions measurements obtained from site-based sensor(s). In some embodiments, the reconciliation circuitry is configured to generate optimized emissions quantification and report based on emissions data associated with the first emissions data acquisition level and emissions data associated with the second emissions data acquisition level.

The reconciliation circuitry 218, includes hardware, software, firmware, and/or a combination thereof, that generates optimized emissions quantification for one or more plants based on emissions data associated with a first emissions data acquisition level and emissions data associated with a second emissions data acquisition level, utilizing a reconciliation model. In some embodiments, the reconciliation circuitry 218 utilizes data, such as current emissions data, historical environmental data, production parameter data, and/or other data associated with one or more component(s) (e.g., physical components(s), assets, and/or the like) in generating an optimized emissions quantification and report. (e.g., as input to the reconciliation model and/or configuration data for the reconciliation model). Additionally and/or alternatively, in some embodiments, the reconciliation circuitry 218 utilizes data associated with a plant, such as historical greenhouse gas emissions data, historical production parameter data, current production parameter data, and/or the like, to predict emissions data for the plant. For example, the reconciliation circuitry 218 may utilize data (e.g., as described above) associated with a plant to generate, for a given time period (e.g., current time period, future time period) predicted first emissions data corresponding to a first emissions data acquisition level, and/or predicted second emissions data corresponding to a second emissions data acquisition level. In some embodiments, historical greenhouse gas emissions data may include, for example, historical greenhouse gas emissions measurements corresponding to past operation of a system under certain operating conditions, emissions amount trend data, and/or the like). In some embodiments, the reconciliation circuitry 218 includes hardware, software, firmware, and/or a combination thereof, that outputs optimized emissions quantification for one or more plants, wherein the optimized emissions quantification reflects reconciled emissions data obtained from multiple sensors and associated with at least two emissions data acquisition levels, such as the first emissions data acquisition level and second emissions data acquisition level described above. In one particular embodiment, the reconciliation circuitry 218 utilizes a reconciliation model that is configured to minimize the difference (e.g., data discrepancy) between aggregated emissions data obtained from source-based sensor(s) associated with the first emissions data acquisition level and emissions data from site-based sensor(s) associated with the second emissions data acquisition level. In some embodiments, the reconciliation circuitry, includes hardware, software, firmware, and/or a combination thereof, that determines data discrepancy between the source-based sensor(s) aggregated emissions data and the site-based sensor emissions data. The source-based sensor aggregated emissions data may correspond to a first emission data for a given period and the sited-based sensor emissions data may correspond to a second emissions data for the given time period, as described above. In some embodiments, data discrepancy may describe a difference between source-based sensor(s) aggregated emissions data (e.g., first emissions data) and site-based sensor emissions data (e.g., second emissions data) that satisfies a difference threshold (e.g., 0 ton, 200 tons, 3000 tons, and/or the like). In some embodiments, the difference threshold is a predetermined threshold. In some embodiments, the difference threshold is configurable. In some embodiments, data discrepancy may be indicative of errors in one or more portions of the emissions data (e.g., error(s) in the emissions data associated with the first emissions data acquisition level and/or error(s) in the emissions data associated with the second emissions data acquisition level). In various embodiments, the reconciliation circuitry 218 is configured to reconcile (e.g., continuously, periodically, predetermined intervals, and/or the like) emissions data comprising first emissions data and second emissions data based at least in part on performing one or more reconciliation operations with respect to the two emissions data. In some embodiments, the one or more reconciliation operations comprise applying a reconciliation algorithm. In some embodiments, the reconciliation algorithm is a predicted and/or projected reconciliation algorithm that may, for example, be predicted using a machine learning model and/or other prediction methods.

In some embodiments, the reconciliation circuitry 218, includes hardware, software, firmware, and/or a combination thereof, that in response to determining data discrepancy between the source-based sensor(s) aggregated emissions data and the site-based sensor emissions data, reconciles the emissions data utilizing the reconciliation model. In some embodiments, reconciling the emissions data comprise tuning, adjusting, or similar words used herein interchangeably, portions of the emissions data based at least in part on weights associated with the respective portions of the emissions data. In some embodiments, the reconciliation circuitry 218 utilizes a reconciliation model embodying a weighted least square-based objective function that comprises weights indicative of the reliability of that portion of the emissions data. In some embodiments, the weights reflect the accuracy of the respective portion of the input emissions data. For example, in some embodiments, emissions data obtained from a given source-based sensor may correspond to a portion of the input emissions data and may be associated with a weight indicative of the reliability of the respective emissions data based at least in part on associated emissions source category and/or sensor type. In some embodiments, emissions data obtained from a site-based sensor may correspond to a portion of the input emissions data and may be associated with a weight indicative of the reliability of the respective emissions data based at least in part on associated emissions source category and/or sensor type. In some embodiments, the weight for a given emissions source category may be determined based at least in part on the measurement accuracy of the sensor and/or measurement technique used in generating the emission data for the emissions source category. Additionally or alternatively, in some embodiments, the weights may be determined based on historical data (e.g., historical emissions data). Additionally and/or alternatively, the reconciliation model may utilize one or more of a variety of AI and/or machine learning techniques in reconciling and/or predicting first emissions data associated with a first emissions data acquisition level and second emissions data associated with a second emissions data acquisition level. In some embodiments, generating the optimized emissions quantification comprises adjusting the input emissions data (e.g., all or portion(s) of the input emissions data) such that one or more model constraints associated with the reconciliation model are satisfied. In some embodiments, examples of the one or more model constraints may include timestamp(s) (e.g., congruent timestamp), tuning and/or calibrating of the measurement devices (e.g., sensors thereof) utilized in measuring, estimating, and/or the like, the first emissions data and the second emissions data. Additionally and/or alternatively, in some embodiments, generating the optimized emissions quantification, utilizing the reconciliation model, comprises performing heuristic analysis with respect to the emissions data. Additionally and/or alternatively, in some embodiments, the reconciliation circuitry 218 includes hardware, software, firmware, and/or a combination thereof, that can predict, using the reconciliation model, future emissions data based at least in part on historical data (e.g., patterns thereof) and can compare the predicted future emissions data with actual emissions so at to determine/detect errors and enables proactive correction of the detected errors.

In some embodiments, the reconciliation model of the reconciliation circuitry 218 includes or otherwise embodies a machine learning model. In some example embodiments, the reconciliation circuitry 218 is associated with a training phase and a prediction phase, wherein the reconciliation model of the reconciliation circuitry 218 is configured based at least in part on a training process and a prediction process. In some embodiments, the reconciliation circuitry 218 is configured to cause (e.g., using AI and machine learning circuitry 220) the reconciliation model to undergo a training process using a training dataset in order to identify features and to determine optimal coefficients representing adjustment or weights to apply with respect to the features in order to produce reconciled emissions data reflected in the training dataset, for example, based on positive and/or negative correlations between extracted features from the historical operational data and extracted features from historical emissions data (e.g., historical emissions measurements calculated from historical data). As such, in some example, the weights for the reconciliation model may be generated during a training phase of the machine learning-based reconciliation model. The reconciliation circuitry 218 may cause the reconciliation model to be trained to generate optimized emissions quantification by learning from the training dataset.

In some embodiments, training the machine learning model may include the machine learning model applying one or more machine learning techniques on the training dataset. In some embodiments, the reconciliation circuitry provides training dataset to the reconciliation model. In some embodiments, the training dataset input into the reconciliation model may comprise historical data for the plant 102, including historical operational data, historical emissions data, and/or simulated data, including simulated operational data and/or simulated emissions data.

In general, operational data for a plant 102 may indicate various properties, detected conditions, user-configured settings, parameters, outputs, and/or measurements corresponding to operation of the plant 102. Operational data may include historical operational data corresponding to past and current operation of the plant 102. Operational data may also include projected or planned operational data corresponding to planned or future operation of the plant 102. Operational data may include preconfigured, calculated, and/or user inputted data associated with operation of the plant 102, including historical, current, and/or projected production parameters. Operational data may include sensor data received via sensors 120 and indicative of various conditions and/or values detected and/or measured during past and/or current operation of the plant 102. In various embodiments the sensor data includes emissions data received via the sensors 102.

Production parameters for a plant may refer to information and/or data for determining or describing how the plant 102, and/or one or more particular assets associated therewith, for example assets embodying physical processing units or other components of a processing plant, operates during various periods of operation of the plant 102. The production parameters may be user-configured and/or user inputted values and/or data objects representing desired functionality or operation of the plant 102 and/or one or more particular assets and/or components thereof. The production parameters may determine the operation of the plant 102 and/or one or more particular assets and/or components thereof. For example, the emissions quantification system 140 and/or a controller of the plant 102 may facilitate reconfiguration of one or more particular assets, sensors, and/or components thereof, for example, based at least in part on the optimized emissions quantification and/or report for the plant 102. The production parameters may describe the operation of the plant 102 and/or one or more particular assets, sensors, and/or components thereof. For example, the plant 102 and/or one or more particular assets, sensors, and/or components thereof may be configured to operate according to the production parameters by means other than the production parameters themselves (e.g., electronically, mechanically, chemically, and/or the like), and the production parameters may be input, generated, and/or retained as a record to describe how the plant 102 and/or one or more particular assets, sensors, and/or components thereof is or was configured to operate during various periods of operation. The production parameters may include data indicative of operating capacity and/or operating modes of a plant 102 and/or one or more particular assets, sensors and/or components thereof during various periods of operation.

The historical operational data may comprise sensor data, including operating conditions data and/or emissions data generated via the one or more sensors 120. The sensor data may include sensor data collected over relatively long periods of time such as one or more years as well as current sensor data (e.g., collected in real time). For example, operating conditions data of the historical operational data 350 may include a timestamp indicating an instance of time when each detection or measurement was taken along with sensor data (e.g., sensor values) indicative of the emissions amount and/or operating conditions at that instance of time such as temperature, pressure, flow rate, and/or composition of materials moving through and/or being processed within or by various components of the plant 102 or of the components of the plant 102 themselves, to list a few examples.

The historical operational data may comprise preconfigured, calculated, and/or user inputted data associated with past operations of one or more plant(s) and/or one or more particular assets, sensors and/or components thereof, including historical and/or current production parameters. Each historical production parameter of the historical operational data may describe how the plant 102 and/or one or more particular assets and/or components thereof is or was configured to operate during periods of operation corresponding to the production parameter, including data indicative of past operating capacity and/or past operating modes of the plant 102 and/or one or more particular assets and/or components thereof.

In one example, the historical production parameters of the historical operational data may include past operating capacity, past operating modes, and/or any other historical production parameters corresponding to one or more periods of past or current operation of the plant 102 and/or one or more particular assets, sensors, and/or components thereof. These historical production parameters may be user-configured and/or user inputted (e.g., originally as projected production parameters) in order to determine how the plant 102 and/or one or more particular assets and/or components thereof is to operate during a period of time and then retained and stored (e.g., as historical production parameters) to provide a historical record describing how the plant 102 and/or one or more particular assets and/or components thereof operated during past operation of the plant 102 during that period of time. The historical production parameters may be combined with, may incorporate, and/or may include references to information and/or data that is determined and/or calculated during the past operation of the plant 102 and/or one or more particular assets, sensors, and/or components thereof and then stored in association with the historical production parameters such as, for example, historical sensor data, including historical operating conditions data and/or the historical emissions data.

The historical emissions data may comprise emissions data generated via one or more sensors 120. A sensor of the one or more sensors may be specifically emissions sensors for measuring emissions of a particular gas (e.g., methane) produced by the plant 102 and/or one or more particular assets and/or components thereof, including individual components of the plant 102, parts of the individual components, groups of components, and/or the plant 102 overall. Additionally or alternatively, a sensor of the one or more sensors may be configured to be used in conjunction with emission factor(s) and/or other methods of emissions estimation to generate an emissions amount. Emissions data may include emissions data collected over relatively long periods of time such as one or more years as well as current sensor data (e.g., collected in real time). In one example, the emissions data may comprise a timestamp indicating an instance of time when each measurement was taken along with attributes characterizing the emissions measurement such as emissions type, quantity, and/or volume of gas emitted at one or more components of the plant 102 and/or for the plant 102 as a whole.

The simulated data may comprise simulated emissions data, simulated production parameters, and/or simulated operating conditions data. The simulated emissions data may indicate estimated emissions for a particular gas that would result from operation of the plant 102 and/or one or more particular assets and/or components thereof according to one or more sets of simulated production parameters. In some embodiments, the simulated emissions data may be generated or caused to be generated by the reconciliation circuitry 218 and/or the AI and machine learning circuitry 220. The simulated emissions data may be generated by a simulation process configured to receive (e.g., via user input) a virtual representation of one or more plant 102 and/or one or more particular assets and/or components thereof and simulated production parameters and, based on the received virtual representation and simulated production parameters, output simulated data representing results of operation of the plant 102 and/or one or more particular assets and/or components thereof according to the simulated production parameters. The simulated data output by the simulation process may comprise simulated emissions data representing estimated emissions of a particular gas (e.g., methane) that would result from the operation of the plant 102 and/or one or more particular assets and/or components thereof according to the simulated production parameters. The simulated data output by the simulation process may comprise simulated operating conditions data representing estimated operating conditions that would result from the operation of the plant 102 and/or one or more particular assets and/or components thereof according to the simulated production parameters, such as estimated temperature, pressure, flow rate, and/or composition of materials moving through and/or being processed within or by various components of the system or of the components themselves, to list a few examples. The simulated production parameters received as input by the simulation process may be preconfigured or user-configured and/or may be selected from sets of possible production parameters associated with each plant 102 and/or one or more particular assets and/or components thereof (and/or each virtual representation of each plant 102 and/or one or more particular assets and/or components thereof).

In some embodiments, the historical operational data, historical emissions data, and simulated data are input into the training process of the reconciliation model to train the model to generate the optimized emissions quantification. In some embodiments, a product of the model training are trained model weights that are used by the prediction process of the reconciliation model. In some embodiments, after an initial training, further training data (e.g., subsequently received and/or generated historical operational data, historical emissions data, simulated data) may be input to the training process of the reconciliation model, periodically or on an on-going basis, to refine and update the model.

In some embodiments (not illustrated), the reconciliation model may comprise one or more specially designed algorithms (e.g., reconciliation algorithm) for generating optimized emissions quantification based at least in part on reconciling input emissions data associated with at least two emissions data acquisition levels and utilizing one or more of weights associated with the emissions data, historical operational data, historical emissions data, simulated data, projected production parameters, or emissions reduction strategy information. For example, in some embodiments, the one or more specially designed algorithms may be configured to determine one or more adjustment values for tuning the received or retrieved input emissions data based at least in part on the weights associated with the input emissions data. Additionally or alternatively, in some embodiments, the one or more specially designed algorithms may be configured to determine one or more adjustment values for tuning the received or retrieved input emissions data based at least in part on the historical operational data, the historical emissions data, and/or simulated data (e.g., via regression analysis). The reconciliation circuitry 218, using the reconciliation model, may generate reconciled emissions data based at least in part on applying the one or more adjustment values to corresponding portion(s) of the input emissions data, and adopt the reconciled emissions data as the optimized emissions quantification. In some embodiments, the reconciliation model may comprise a reconciliation algorithm that is a predicted reconciliation algorithm (e.g., predicted using a machine learning model and/or other prediction methods).

In some embodiments, the reconciliation circuitry 218 includes a separate processor, specially configured field programmable gate array (FPGA), or a specially programmed application specific integrated circuit (ASIC).

In some embodiments, two or more of the sets of circuitries 202-208, and 212-222 are combinable. Alternatively, or additionally, one or more of the sets of circuitry 202-208, and 212-222 perform some or all of the operations and/or functionality described herein as being associated with another circuitry. In some embodiments, two or more of the sets of circuitry 202, 208, and 212-222 are combined into a single module embodied in hardware, software, firmware, and/or a combination thereof. For example, in some embodiments, one or more of the sets of circuitry, for example the AI and machine learning circuitry 220, may be combined with the processor 202, such that the processor 202 performs one or more of the operations described herein with respect the AI and machine learning circuitry 220.

Example Computer-Implemented Processes

Having described example systems, apparatuses, data architectures, and model implementations in accordance with the present disclosure, example processes for generating an optimized emissions quantification will now be discussed. It will be appreciated that each of the flowcharts depicts an example computer-implemented process that is performable by one or more of the apparatuses, systems, devices, and/or computer program products described herein, for example utilizing one or more of the specially configured components thereof.

The blocks indicate operations of each process. Such operations may be performed in any of a number of ways, including, without limitation, in the order and manner as depicted and described herein. In some embodiments, one or more blocks of any of the processes described herein occur in-between one or more blocks of another process, before one or more blocks of another process, in parallel with one or more blocks of another process, and/or as a sub-process of a second process. Additionally or alternatively, any of the processes in various embodiments include some or all operational steps described and/or depicted, including one or more optional blocks in some embodiments. With regard to the flowcharts illustrated herein, one or more of the depicted block(s) in some embodiments is/are optional in some, or all, embodiments of the disclosure. Optional blocks are depicted with broken (or "dashed") lines. Similarly, it should be appreciated that one or more of the operations of each flowchart may be combinable, replaceable, and/or otherwise altered as described herein.

In some embodiments, an optimized emissions quantification and/or report is generated utilizing a reconciliation model. In some embodiments, generating an optimized emissions quantification utilizing a reconciliation model may comprise performing one or more configuration operations. FIG. 3 illustrates a flowchart including example operations of an example process for performing configuration operation(s) associated with generating optimized emissions quantification utilizing a reconciliation model. Specifically, FIG. 3 illustrates an example computer-implemented process 300. In some embodiments, the process 300 is embodied by computer program code stored on a non-transitory computer-readable storage medium of a computer program product configured for execution to perform the process as depicted and described. Alternatively or additionally, in some embodiments, the process 300 is performed by one or more specially configured computing devices, such as the apparatus 200 alone or in communication with one or more other component(s), device(s), system(s), and/or the like. In this regard, in some such embodiments, the apparatus 200 is specially configured by computer-coded instructions (e.g., computer program instructions) stored thereon, for example in the memory 204 and/or another component depicted and/or described herein and/or otherwise accessible to the apparatus 200, for performing the operations as depicted and described. For example, the apparatus 200 in some embodiments is in communication with separate physical component(s) of one or more industrial plants, and/or the like. For purposes of simplifying the description, the process 300 is described as performed by and from the perspective of the apparatus 200.

The process 300 begins at operation 302 at which an apparatus (such as, but not limited to, the apparatus 200 or circuitry thereof as described above in connection with FIG. 2) generates a reconciliation model. In some embodiments, generating the reconciliation model may comprise defining an objective function. In some embodiments, defining the objective function comprises specifying one or more objective values and/or relationship between the one or more objective values. The objective function may be defined/determined such that the reconciliation model generates reconciled emissions data for a first emissions data and second emissions data associated with a given time period, wherein the difference between the first emissions data and second emissions data is minimized. In some embodiments, the reconciliation model may be configured to optimize the objective function in accordance with one or more model constraints.

At operation 304, an apparatus (such as, but not limited to, the apparatus 200 or circuitry thereof as described above in connection with FIG. 2) generates weight(s) for the reconciliation model. In some embodiments, the reconciliation model may be configured to reconcile emissions data based at least in part on associated weights. For example, in some embodiments, a weight may be generated for, or otherwise assigned, to each emissions source category of a plurality of emissions source categories associated with a plant. In some embodiments, the reconciliation model employs an objective function that incorporates the weights. For example, in some embodiments, the reconciliation model may embody a weighted least square-based objective function incorporating the weights.

In some embodiments, the weight for a given emissions source category may be generated based at least in part on the accuracy of the measurement technique and/or sensor type associated with the emissions source category (e.g., the measurement technique and/or sensor type used in quantifying (measuring, estimating) emissions data for the emissions source category. As such, in some embodiments, the weight for a given portion of emissions data may comprise a reliability weight that is indicative of the accuracy of the portion of the emissions data.

In some embodiments, machine learning technique(s) may be employed to determine/generate the weights for the reconciliation model. For example, in some embodiments, the reconciliation model may be trained based on a training dataset to determine/generate the weights. The training dataset may comprise historical emissions data, historical operational data, and/or simulated data.

At operation 306, an apparatus (such as, but not limited to, the apparatus 200 or circuitry thereof as described above in connection with FIG. 2) updates the reconciliation model. In some embodiments, updating the reconciliation model comprises updating the weights for the reconciliation model. In some embodiments, the weights may be updated based at least in part on trends with respect to the effect of the optimized emissions quantification over a period of time.

FIG. 4 illustrates a flowchart including operational blocks of an example process 400 for generating optimized emissions quantification in accordance with at least one example embodiments of the present disclosure. In some embodiments, the noted example process 400 may be performed subsequent to performing one or more configuration operations (e.g., as described above in relation to FIG. 3). Specifically, FIG. 4 illustrates an example computer-implemented process 400. In some embodiments, the process 400 is embodied by computer program code stored on a non-transitory computer-readable storage medium of a computer program product configured for execution to perform the process as depicted and described. Alternatively or additionally, in some embodiments, the process 400 is performed by one or more specially configured computing devices, such as the apparatus 200 alone or in communication with one or more other component(s), device(s), system(s), and/or the like. In this regard, in some such embodiments, the apparatus 200 is specially configured by computer-coded instructions (e.g., computer program instructions) stored thereon, for example in the memory 204 and/or another component depicted and/or described herein and/or otherwise accessible to the apparatus 200, for performing the operations as depicted and described. In some embodiments, the apparatus 200 is in communication with one or more external apparatus(es), system(s), device(s), and/or the like, to perform one or more of the operations as depicted and described. For example, the apparatus 200 in some embodiments is in communication with separate physical component(s) of one or more plants, and/or the like. For purposes of simplifying the description, the process 400 is described as performed by and from the perspective of the apparatus 200.

The process begins at operation 402, at which an apparatus (such as, but not limited to, the apparatus 200 or circuitry thereof as described above in connection with FIG. 2) receives emissions data associated with one or more plants 102, such as the plant depicted in FIG. 1. In some embodiments, the emissions data reflects emissions data for a particular individual gas. In some embodiments, the emissions data reflects unified emissions data for multiple gases. Additionally, in some embodiments, the apparatus may receive operational data associated with the one or more plants 102. In one example, the apparatus may be configured to gather, request, receive, and/or aggregate time series emissions data. Additionally, in the noted example, the apparatus may be configured to gather, request, receive, and/or aggregate time series operational data and from one or more plants 102, over a period of time, wherein the time serious operational data correspond to the time series emissions data with respect to the timestamp. In some examples, the apparatus may be configured to store the gathered, requested, received, and/or aggregated data.

At operation 404, an apparatus (such as, but not limited to, the apparatus 200 or circuitry thereof described above in connection with FIG. 2) identifies first emissions data and second emissions data associated with the one or more plants based on the received emissions data. In some embodiments, the first emissions data is associated with a first emissions data acquisition level of a plurality of emissions data acquisition levels, such as the first emissions data acquisition level described above in connection with FIGS. 1 and 2. In some embodiments, the second emissions data is associated with a second emissions data acquisition level of the plurality of emissions data acquisition levels, such as the second emissions data acquisition level described above in connection with FIGS. 1 and 2. In some embodiments, the apparatus is configured to identify a first emissions data and a second emissions data that are associated with substantially the same timestamp (e.g., day, month, year). For example, the apparatus may be configured to find matching first emissions data and second emissions data with respect to associated timestamp. In some examples, the first emissions data comprises a set of source-based emissions data generated based at least in part on one or more source-based sensors, wherein each data value in the set of source-based emissions data is associated with an emissions source category of a plurality of emissions source categories for the plant. Each data value in the set of source-based emissions data may correspond to a portion of the first emissions data. In some examples, an aggregate of the set of source-based emissions data represents a total emissions (e.g., first total emissions) for the plant based on using emissions quantification (e.g., measuring, estimating) techniques and/or sensors (e.g., one or more of sensors 120) associated with the first emissions data acquisition level. In some examples, the second emissions data comprises site-based emissions data and represents a total emissions (e.g., second total emissions for the plant) based on using emissions quantification techniques and/or sensors (such as one or more of the sensors 120) associated with the second emissions data acquisition level. In some embodiments, the operation 404 may be performed in according to the example process 500 that is depicted in FIG. 5, which is an example process for identify matching emissions data (e.g., first emissions data, second emissions data) for a given time period.

The process 500 begins at operation 502, at which an apparatus (such as, but not limited to, the apparatus 200 or circuitry thereof as described above in connection with FIG. 2) identifies, for a given time period, second emissions data from the received emissions data. The second emissions data may comprise site-based emissions data, as described above (e.g., emissions data obtained using site-based sensors, such as satellites, drones, and/or the like).

At operation 504, an apparatus (such as, but not limited to, the apparatus 200 or circuitry thereof as described above in connection with FIG. 2) determines a timestamp (e.g., day, month, year) associated with the second emissions data.

At operation 506, an apparatus (such as, but not limited to, the apparatus 200 or circuitry thereof as described above in connection with FIG. 2) identifies first emissions data from the received emissions data based on the timestamp associated with the second emissions data. For example, the apparatus may parse the received emissions data to identify emissions data associated with the first emissions data acquisition level for the given time period and having a timestamp that is substantially the same as the timestamp for the second emissions data for the given time period. For example, if the timestamp identified for the second emissions data is Jan. 10, 2020, the apparatus 200 may be configured to parse through the emissions data associated with first emissions data acquisition level for the given time period, and identify the emissions having a Jan. 10, 2020 as the second emissions data.

Alternatively, in some embodiments, the apparatus identifies first emissions data from the received emissions data, and determines a timestamp (e.g., day, month, year) associated with the first emissions data. The apparatus may then identify second emissions data from the received emissions data based on the timestamp associated with the first emissions data. For example, the apparatus may parse the received emissions data to identify emissions data associated with the second emissions data acquisition level for a given time period and having a timestamp that is substantially the same as the timestamp for the first emissions data for the given time period.

Returning to FIG. 4 at operation 406, an apparatus (such as, but not limited to, the apparatus 200 or circuitry thereof described above in connection with FIG. 2) generates, using a reconciliation model (such as, but not limited to, the reconciliation model described above in connection with FIG. 2), optimized emissions quantification for the one or more plants based on the first emissions data and the second emissions data. For example, in some embodiments, the apparatus may apply the reconciliation model to the first emissions data and the second emissions model to minimize the difference between the first emissions data and the second emissions data, such that effect of errors in the emissions data is reduced. The optimized emissions quantification may correspond to a period of time associated with the emissions data, for example the first and second emissions data thereof. In some embodiments where operational data is employed, the optimize emissions quantification may correspond to a period of time associated with the operational data. For example, the emissions data, the operational data, and the generated optimized emissions quantification may correspond to the same period of time.

In some embodiments, the apparatus, using the reconciliation model, may be configured to generate the optimized emissions quantification in accordance with the example process 600 that is depicted in FIG. 6, which is an example process for generation optimized emissions quantification based on a different measure. The process 600 begins at operation 602, at which an apparatus (such as, but not limited to, the apparatus 200 or circuitry thereof as described above in connection with FIG. 2) determines a difference measure between the first emissions data and the second emissions data. In this regard, a difference measure may describe the difference between the first emissions data (e.g., aggregated set of source-based emissions data representing a first total emissions for the plant) and the second emissions data (e.g., single site-based emissions data representing a second total emissions for the plant).

At operation 604, an apparatus (such as, but not limited to, the apparatus 200 or circuitry thereof as described above in connection with FIG. 2) determines whether the difference measure is a qualifying difference measure. A qualifying difference measure may describe a difference measure between the first emissions data and the second emissions data that satisfies a difference threshold (e.g., as described above).

At operation 606, an apparatus (such as, but not limited to, the apparatus 200 or circuitry thereof as described above in connection with FIG. 2) responsive to determining that the difference measure is a qualifying difference measure, generates the optimized emissions quantification based at least in part on the difference measure. In some embodiments, generating an optimized emissions quantification based at least in part on the difference measure comprises applying the difference measure to the first emissions data. In some embodiments, generating an optimized emissions quantification based at least in part on the difference measure comprises applying the difference measure to the second emissions data. In some embodiments, generating an optimized emissions quantification based at least in part on the difference measure comprise applying a first portion of the difference measure to the first emissions data and applying a second portion of the difference measure to the second emissions data.

In some embodiments, applying the difference measure or portion(s) of the difference measure to the emissions data (e.g., first emissions data, second emissions data) comprises altering the emissions data based at least in part on the difference measure or otherwise combining the difference measure with the emissions data in a manner that accounts for error in the emissions data (e.g., measurement errors, such as random errors and gross errors). For example, in some embodiments applying the difference measure to the input emissions data may comprise distributing the difference measure across portions of the emissions data. For example, in some embodiments the difference measure is distributed between the first emissions data and the second emissions data. As another example, in some embodiments the difference measure is distributed only across the first emissions data. In some embodiments, the difference measure or portions thereof is applied to the first emissions data, or applied to the second emissions data based on the weight(s) associated with the first emissions data and/or the weight(s) associated with the second emissions data. For example, in some embodiments, to apply the difference measure to the first emissions data, the apparatus, using the reconciliation model, distributes the difference measure across the set of emissions data embodied by the first emissions data based at least in part on the weights associated with each data value in the set of emissions data.

Returning to FIG. 4 at operation 408, an apparatus (such as, but not limited to, the apparatus 200 or circuitry thereof described above in connection with FIG. 2) generates an emissions report reflecting the optimized emissions quantification. In some embodiments, the emissions report may embody a prediction-based action (e.g., the performance of which may be initiated by the apparatus 200). In some embodiments, the emissions report may comprise adjusted first emissions data and/or adjusted second emissions data. For example, in some embodiments, the emissions report is generated to include the optimized emissions quantification as a particular parameter value that replaces one or more portions of the first emissions data and/or second emissions data that are reconciled.

At operation 410, an apparatus (such as, but not limited to, the apparatus 200 or circuitry thereof described above in connection with FIG. 2) initiates the performance of one or more prediction-based actions based at least in part on the optimized emissions quantification. In some embodiments, initiating the performance of one or more prediction-based actions comprises generating an emissions report based on the optimized emissions quantification. In some embodiments, initiating the one or more prediction-based actions comprises outputting the optimized emissions quantification. In some embodiments, the apparatus outputs the optimized emissions quantification via a display of the apparatus, for example by causing rendering of user interface (e.g., output user interface) via the apparatus. Additionally or alternatively, in some embodiments, the apparatus outputs the optimized emissions quantification via at least one transmission to a client device to cause the client device to cause rendering of a user interface including or otherwise associated with the optimized emissions quantification. Additionally or alternatively, in some embodiments, the apparatus outputs the optimized emissions quantification for subsequent downstream processing. In some embodiments, the apparatus outputs the optimized emissions quantification by transmitting the optimized emissions quantification for use and/or further processing by an external device, system, and/or the like. In some embodiments, the apparatus outputs the optimized emissions quantification for use in automatically configuring/reconfiguring operation one or more sensors, component(s), and/or assets of the corresponding one or more plants, based at least in part on the generated optimized emissions quantification.

In some embodiments, at least a portion of the optimized emissions quantification is outputted for use with at least one plant-wide optimization process. For example, in some embodiments the apparatus 200 outputs the at least a portion of the optimized emissions quantification by applying the at least a portion of the optimized emissions quantification to a plant-wide optimization process.

In some embodiments, one or more operations of the process 400 may be performed periodically (e.g., every month, every 2 months, and/or the like). Additionally and/or alternatively, in some embodiments, one or more operations of the process 400 is/are performed in response to one or more data-driven trigger(s), for example particular detected timestamp(s), detected data value(s) and/or associated threshold(s), receiving of user input requesting to initiate the process 400, and/or the like. Additionally and/or alternating one or more operations of the process 400 may be performed in response to one or more changes/updates, (e.g., changes in the operation of the plant, update sensors, and/or the like). In some embodiments, each execution of the noted one or more operations of the process 400 may comprise a model execution cycle, wherein the output of an executed cycle is an optimized emissions quantification that is generated based at least in part on current input emissions data.

FIG. 7 provides an operational example showing an output user interface 700 that may be generated by the emissions quantification system 140 and/or the user device 160 based at least in part on the optimized emissions quantification. In some embodiments, the user interface 700 embodies a user interface configured to be rendered to a native application associated with the emissions quantification system 140, the user device 160, and/or another computing device, for example (e.g., using the data output circuitry 214). In some embodiments, the user interface 700 embodies a web interface accessible by a browser or other web application (e.g., via the data output circuitry 214). In this regard, for example, the user interface 700 may be accessible by a browser or other web application associated with the emissions quantification system 140, the user device 160, and/or another computing device.

In some embodiments, the user interface 700 may be configured to display the emissions report 702. In some embodiments, generating the user interface 700 includes generating interface components with each interface component configured to automatically display a corresponding section of the plurality of sections of the emissions report 702. For example, the interface components may include input emissions data interface component 704 and optimized emissions quantification interface component 706. As depicted in FIG. 7, each of the input emissions data component and the optimized emissions quantification component may be configured to automatically display the source-based emissions data component 708, 710 along with the emissions source category 712, 714, the corresponding emissions amount 716, 718, and the aggregated emissions amount 728, 730 representing a total amount of emissions corresponding to a first emissions data acquisition level. As further depicted in FIG. 7, each of the input emissions data component and the optimized emissions quantification component may be configured to automatically display the site-based emissions data component 720, 722 along with the corresponding emissions amount 724, 726 representing a total amount corresponding to a second emissions data acquisition level.

In some embodiments, the emissions quantification system 140 and/or the user device 160 may be configured to update the user interface 700. In this regard, for example, the emissions values associated with the input emissions data component and the optimized emissions quantification component may be updated. In some embodiments, the user interface 700 may be updated via user selection. For example, a user may update the user interface 700 via update component 734. In some embodiments, the user interface 700 may be updated in real-time. For example, the user interface 700 may be updated as input emissions data is received by the emissions quantification system 140 and/or the user device 160. In some embodiments, the user interface 700 may be updated on a periodic basis. For example, the user interface 700 may be updated once per week, once per month, once per quarter, once per year, and/or the like.

CONCLUSION

Although example processing systems have been described in the figures herein, implementations of the subject matter and the functional operations described herein can be implemented in other types of digital electronic circuitry, or in computer software, firmware, or hardware, including the structures disclosed in this specification and their structural equivalents, or in combinations of one or more of them.

Embodiments of the subject matter and the operations described herein can be implemented in digital electronic circuitry, or in computer software, firmware, or hardware, including the structures disclosed in this specification and their structural equivalents, or in combinations of one or more of them. Embodiments of the subject matter described herein can be implemented as one or more computer programs, i.e., one or more modules of computer program instructions, encoded on computer storage medium for execution by, or to control the operation of, information/data processing apparatus. Alternatively, or in addition, the program instructions can be encoded on an artificially-generated propagated signal, e.g., a machine-generated electrical, optical, or electromagnetic signal, which is generated to encode information/data for transmission to suitable receiver apparatus for execution by an information/data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described herein can be implemented as operations performed by an information/data processing apparatus on information/data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a repository management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or information/data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communications network.

The processes and logic flows described herein can be performed by one or more programmable processors executing one or more computer programs to perform actions by operating on input information/data and generating output. Processors suitable for the execution of a computer program include, by way of example, both general and special purpose microprocessors, and any one or more processors of any kind of digital computer. Generally, a processor will receive instructions and information/data from a read-only memory or a random access memory or both. The essential elements of a computer are a processor for performing actions in accordance with instructions and one or more memory devices for storing instructions and data. Generally, a computer will also include, or be operatively coupled to receive information/data from or transfer information/data to, or both, one or more mass storage devices for storing data, e.g., magnetic, magneto-optical disks, or optical disks. However, a computer need not have such devices. Devices suitable for storing computer program instructions and information/data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described herein can be implemented on a computer having a display device, e.g., a CRT (cathode ray tube) or LCD (liquid crystal display) monitor, for displaying information/data to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described herein can be implemented in a computing system that includes a back-end component, e.g., as an information/data server, or that includes a middleware component, e.g., an application server, or that includes a front-end component, e.g., a client computer having a graphical user interface or a web browser through which a user can interact with an implementation of the subject matter described herein, or any combination of one or more such back-end, middleware, or front-end components. The components of the system can be interconnected by any form or medium of digital information/data communication, e.g., a communications network. Examples of communications networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and typically interact through a communications network. The relationship of client and server arises by virtue of computer programs running on the respective computers and having a client-server relationship to each other. In some embodiments, a server transmits information/data (e.g., an HTML page) to a client device (e.g., for purposes of displaying information/data to and receiving user input from a user interacting with the client device). Information/data generated at the client device (e.g., a result of the user interaction) can be received from the client device at the server.

While this specification contains many specific implementation details, these should not be construed as limitations on the scope of any disclosures or of what may be claimed, but rather as descriptions of features specific to particular embodiments of particular disclosures. Certain features that are described herein in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

It is to be understood that the disclosure is not to be limited to the specific embodiments disclosed, and that modifications and other embodiments are intended to be included within the scope of the appended claims. Although specific terms are employed herein, they are used in a generic and descriptive sense only and not for purposes of limitation, unless described otherwise.

What is claimed is:

1. A computer-implemented method comprising:

receiving, from one or more sensors associated with one or more measuring devices of a plant, data indicative of emissions associated with the plant;

identifying, based on the received data, a first emissions data and a second emissions data, wherein the first emissions data is associated with first emissions data acquisition level of a plurality of emissions data acquisition levels and the second emissions data is associated with a second emissions data acquisition level of the plurality of emissions data acquisition levels, wherein the identification of the first emissions data and the second emissions data comprises parsing the received data to identify emissions data associated with the second emissions data acquisition level for a time period as the second emissions data, and identifying the first emissions data from the emissions data based on a timestamp associated with the second emissions data;

determining, by a reconciliation model, based on the first emissions data and the second emissions data, one or more adjustment values for one or more portions of the first emissions data or one or more portions of the second emissions data, wherein the one or more adjustment values are determined based on a historical operational data;

applying the one or more adjustment values to the one or more portions of the first emissions data or the one or more portions of the second emissions data to generate optimized emissions quantification;

generating, based on the one or more adjustment values, the optimized emissions quantification, wherein the optimized emissions quantification reflects reconciled emissions data with respect to the first emissions data and the second emissions data;

transmitting, based on the optimized emissions quantification, one or more commands to at least one computing device associated with the plant; and initiating performance of one or more prediction-based actions by executing the one or more commands by the least one computing device, wherein the execution of the one or more commands controls one or more operations of the plant.

2. The computer-implemented method of claim 1, wherein initiating the performance of the one or more prediction-based actions comprises:

generating an emissions report based on the optimized emissions quantification.

3. The computer-implemented method of claim 1, wherein the first emissions data and the second emissions data are associated with substantially the same timestamp.

4. The computer-implemented method of claim 1, wherein generating the optimized emissions quantification comprises:

determining a difference measure between the first emissions data and the second emissions data; and responsive to determining that the difference measure is a qualifying difference measure, generating the optimized emissions quantification based on the difference measure.

5. The computer-implemented method of claim 4, wherein generating the optimized emissions quantification based on the difference measure comprises:

applying the difference measure to the first emissions data.

6. The computer-implemented method of claim 4, wherein generating the optimized emissions quantification based on the difference measure comprises:

applying a first portion of the difference measure to the first emissions data; and applying a second portion of the difference measure to the second emissions data.

7. The computer-implemented method of claim 5, wherein applying the difference measure to the first emissions data comprises:

applying the difference measure to one or more portions of the first emissions data based at least in part on weights associated with the one or more portions of the first emissions data.

8. The computer-implemented method of claim 1, wherein:

the first emissions data comprises a set of source-based emissions data, each data value in the set of source-based emissions data is associated with an emissions source category of a plurality of emissions source categories for the plant and corresponds to a portion of the first emissions data, and an aggregate of the set of source-based emissions data represents a first total emissions for the plant.

9. The computer-implemented method of claim 8, wherein the second emissions data comprise site-based emissions data and represents a second total emissions for the plant.

10. The computer-implemented method of claim 1, wherein the reconciliation model comprises a machine learning model trained based at least in part on one or more of historical operational data or historical emissions data.

11. An apparatus comprising at least one processor and at least one non-transitory memory comprising program code stored thereon, wherein the at least one non-transitory memory and the program code are configured to, with the at least one processor, cause the apparatus to at least:

receive from one or more sensors associated with one or more measuring devices of a plant, data indicative of emissions associated with the plant;

identify based on the received data, a first emissions data and a second emissions data, wherein the first emissions data is associated with first emissions data acquisition level of a plurality of emissions data acquisition levels and the second emissions data is associated with a second emissions data acquisition level of the plurality of emissions data acquisition levels, wherein the identification of the first emissions data and the second emissions data comprises parsing the received data to identify emissions data associated with the second emissions data acquisition level for a time period as the second emissions data, and identifying the first emissions data from the emissions data based on a time-stamp associated with the second emissions data;

determine by a reconciliation model, based on the first emissions data and the second emissions data, one or more adjustment values for one or more portions of the first emissions data or one or more portions of the second emissions data, wherein the one or more adjustment values are determined based on a historical operational data;

apply the one or more adjustment values to the one or more portions of the first emissions data or the one or more portions of the second emissions data to generate optimized emissions quantification;

generate, based on the one or more adjustment values, the optimized emissions quantification, wherein the optimized emissions quantification reflects reconciled emissions data with respect to the first emissions data and the second emissions data;

transmit based on the optimized emissions quantification, one or more commands to at least one computing device associated with the plant; and initiate performance of one or more prediction-based actions by executing the one or more commands by the least one computing device, wherein the execution of the one or more commands controls one or more operations of the plant.

12. The apparatus of claim 11, wherein the at least one non-transitory memory and the program code are configured to, with the at least one processor, to initiate the performance of the one or more prediction-based actions by generating an emissions report based on the optimized emissions quantification.

13. The apparatus of claim 11, wherein the first emissions data and the second emissions data are associated with substantially the same timestamp.

14. The apparatus of claim 11, wherein the at least one non-transitory memory and the program code are configured to, with the at least one processor, cause the apparatus to generate the optimized emissions quantification using the reconciliation model comprises:

determining a difference measure between the first emissions data and the second emissions data; and responsive to determining that the difference measure is a qualifying difference measure, generating the optimized emissions quantification based on the difference measure.

15. The apparatus of claim 14, wherein the at least one non-transitory memory and the program code are configured to, with the at least one processor, cause the apparatus to generate the optimized emissions quantification based on the difference measure comprises:

applying the difference measure to the first emissions data.

16. The apparatus of claim 14, wherein the at least one non-transitory memory and the program code are configured to, with the at least one processor, cause the apparatus to generate the optimized emissions quantification based on the difference measure comprises:

applying a first portion of the difference measure to the first emissions data; and applying a second portion of the difference measure to the second emissions data.

17. The apparatus of claim 15, wherein applying the difference measure to the first emissions data comprises:

applying the difference measure to one or more portions of the first emissions data based at least in part on reliability weights associated with the one or more portions of the first emissions data.

18. A computer program product comprising at least one non-transitory computer-readable storage medium having computer-readable program code portions stored therein, the computer-readable program code portions comprising an executable portion configured to:

receive, from one or more sensors associated with one or more measuring devices of a plant, data indicative of emissions associated with the plant;

identify, based on the received data, a first emissions data and a second emissions data, wherein the first emissions data is associated with first emissions data acquisition level of a plurality of emissions data acquisition levels and the second emissions data is associated with a second emissions data acquisition level of the plurality of emissions data acquisition levels, wherein the identification of the first emissions data and the second emissions data comprises parsing the received data to identify emissions data associated with the second emissions data acquisition level for a time period as the second emissions data, and identifying the first emissions data from the emissions data based on a time-stamp associated with the second emissions data;

determine, by a reconciliation model, based on the first emissions data and the second emissions data, one or more adjustment values for one or more portions of the first emissions data or one or more portions of the second emissions data, wherein the one or more adjustment values are determined based on a historical operational data;

apply the one or more adjustment values to the one or more portions of the first emissions data or the one or more portions of the second emissions data to generate optimized emissions quantification;

generate, based on the one or more adjustment values, the optimized emissions quantification, wherein the optimized emissions quantification reflects reconciled emissions data with respect to the first emissions data and the second emissions data;

transmit based on the optimized emissions quantification, one or more commands to at least one computing device associated with the plant; and initiate performance of one or more prediction-based actions by executing the one or more commands by the least one computing device, wherein the execution of the one or more commands controls one or more operations of the plant.

* * * * *